United States Patent
Province et al.

(10) Patent No.: US 7,308,305 B1
(45) Date of Patent: Dec. 11, 2007

(54) OPTIMALLY TIMED EARLY SHOCK DEFIBRILLATION

(75) Inventors: Rose Province, San Jose, CA (US); Mark W. Kroll, Crystal Bay, MN (US)

(73) Assignee: Pacesetter, Inc., Sylmar, CA (US)

( * ) Notice: Subject to any disclaimer, the term of this patent is extended or adjusted under 35 U.S.C. 154(b) by 381 days.

(21) Appl. No.: 10/901,480

(22) Filed: Jul. 27, 2004

(51) Int. Cl.
*A61N 1/39* (2006.01)
(52) U.S. Cl. .................................................. 607/5
(58) Field of Classification Search ............... None
See application file for complete search history.

(56) References Cited

U.S. PATENT DOCUMENTS

| | | | |
|---|---|---|---|
| 4,712,555 A | 12/1987 | Thornander et al. | 128/419 PG |
| 4,788,980 A | 12/1988 | Mann et al. | 128/419 PG |
| 4,940,052 A | 7/1990 | Mann et al. | 128/419 PG |
| 4,944,298 A | 7/1990 | Sholder | 128/419 PG |
| 4,996,984 A * | 3/1991 | Sweeney | 607/5 |
| 4,998,974 A | 3/1991 | Aker | 128/419 PG |
| 4,998,975 A | 3/1991 | Cohen et al. | 128/419 D |
| 5,184,616 A | 2/1993 | Weiss | 128/419 |
| 5,224,475 A | 7/1993 | Berg et al. | 128/419 D |
| 5,344,430 A | 9/1994 | Berg et al. | 607/8 |
| 5,466,254 A | 11/1995 | Helland | 607/123 |
| 5,476,483 A | 12/1995 | Bornzin et al. | 607/17 |
| 5,534,019 A | 7/1996 | Paspa | 607/38 |
| 5,578,062 A * | 11/1996 | Alt et al. | 607/5 |
| 5,620,469 A * | 4/1997 | Kroll | 607/7 |
| 5,620,477 A | 4/1997 | Pless et al. | 607/37 |
| 5,709,710 A * | 1/1998 | Armstrong | 607/5 |
| 5,853,426 A * | 12/1998 | Shieh | 607/5 |
| 5,913,887 A | 6/1999 | Michel | 607/123 |
| 5,978,705 A | 11/1999 | KenKnight et al. | 607/5 |
| 6,041,256 A | 3/2000 | Michel | 607/5 |
| 6,167,305 A | 12/2000 | Cammilli et al. | 607/5 |
| 6,314,323 B1 | 11/2001 | Ekwall | 607/23 |
| 6,438,418 B1 | 8/2002 | Swerdlow et al. | 607/5 |
| 6,456,876 B1 | 9/2002 | Kroll | 607/4 |
| 6,539,256 B1 | 3/2003 | KenKnight et al. | 607/5 |
| 2002/0042631 A1 | 4/2002 | Michel | 607/5 |
| 2002/0103507 A1* | 8/2002 | Helland | 607/5 |

FOREIGN PATENT DOCUMENTS

EP          0641573 B1    8/1994

(Continued)

OTHER PUBLICATIONS

James N. Weiss et al., "Ventricular Fibrillation—How Do We Stop the Waves From Breaking?" *Circulation Research*, 2002; vol. 87, pp. 1103-1107.

(Continued)

*Primary Examiner*—Kristen Droesch Mullen

(57) ABSTRACT

An exemplary method includes detecting two or more event interval times associated with an arrhythmic condition, averaging event interval times to provide an average event interval time, providing a fraction and calling for delivery of an anti-arrhythmia shock at a delivery time based on the fraction and the average event interval time. In this exemplary method, the events optionally correspond to early coarse ventricular fibrillation events and the delivery time is optionally less than about three seconds from the detecting of a first event of a first event interval time. Other exemplary methods, devices, systems, etc., are also disclosed.

21 Claims, 15 Drawing Sheets

FOREIGN PATENT DOCUMENTS

| | | |
|---|---|---|
| WO | WO 98/40122 | 9/1998 |
| WO | WO 03/071945 A1 | 9/2003 |

OTHER PUBLICATIONS

Samuel Lévy MD et al., "Low-Energy Cardioversion of Spontaneous Atrial Fibrillation—Immediate and Long-Term Results," *Circulation*, 1997; vol. 96, No. 1, pp. 253-259.

Gust H. Bardy MD, et al., "A Prospective Randomized Repeat-Crossover Comparison of Antitachycardia Pacing With Low-Energy Cardioversion," *Circulation*, 1993; vol. 87, No. 6, pp. 1889-1896.

Sitabhra Sinha et al., "Critical Role of Inhomogeneities in Pacing Termination of Cardiac Reentry," *CHAOS*, 2002; vol. 12, No. 3, pp. 893-902.

* cited by examiner

CONVENTIONAL CIRCUIT AND PERFORMANCE — 600

CONVENTIONAL H-BRIDGE — 610

CONVENTIONAL DISCHARGE — 620

$q = q_o * EXP(-t/RC)$

EXEMPLARY CIRCUIT AND PERFORMANCE ⟵ 700

EXEMPLARY H-BRIDGE ⟵ 710

⟵ 720

EXEMPLARY DISCHARGE $q = q_o * EXP(-t/RC)$

EXEMPLARY SCENARIO FOR EARLY SHOCK
(E.G., NO STORED CHARGE)

- D   DETERMINE NEED FOR SHOCK AND OPTIONALLY START CHARGING CAPACITOR(S)
- S   START CHARGING CAPACITOR(S) FOR HV SHOCK
- F   FULLY CHARGED CAPACITOR(S)
- ΔES   EARLY SHOCK WINDOW (E.G., ~ 2.5 S)

$ALERT_{MAX}$ ~ 7.5 S

EXEMPLARY METHOD 1400

AVERAGE EVENT INTERVAL TIME

EXEMPLARY METHOD

AVERAGE EVENT INTERVAL TIME

EXEMPLARY EQUATION ← 1440

EARLIEST TIME = INT * N + X * INT

N - NUMBER OF INTERVALS

EXEMPLARY SCENARIOS ← 1450

SCENARIO A

INT = 250 MS
N = 3
X = 0.2

EARLIEST TIME = 800 MS

SCENARIO B

INT = 150 MS
N = 3
X = 0.8

EARLIEST TIME = 570 MS

OPTIMALLY TIMED EARLY SHOCK DEFIBRILLATION

RELATED APPLICATIONS

This application is related to U.S. patent applications: 1) Ser. No. 10/901,403, filed Jul. 27, 2004, now U.S. Pat. No. 7,181,276 entitled "Device and Method for Preventing the Acceleration of Cardiac Arrhythmias" to Province and Fayram; 2) Ser. No. 10/901,421, filed Jul. 27, 2004, entitled "Optimized Pathways to Early Shock Defibrillation" to Province and Kroll; and 3) Ser. No. 10/848,853, filed May 18, 2004 now U.S. Pat. No. 7,225,014, entitled "Anti-Arrhythmia Therapy Based on Spatial and/or Temporal Information" to Province. All applications are incorporated herein by reference.

TECHNICAL FIELD

Exemplary methods, devices, systems, etc., presented herein generally relate to early shock defibrillation therapies.

BACKGROUND

Conventional implanted cardiac defibrillation devices (ICDs) are typically programmed to deliver a defibrillation shock only after a device's capacitors have been fully charged. For high voltage shocks, charge times may exceed 10 seconds. For example, a conventional ICD can achieve a stored energy charge of 25 J in about 10 seconds, which is sufficient to deliver a high voltage shock (e.g., leading edge of about 800 V).

While high voltage shocks have proven effective for ventricular defibrillation, the delay between detection of an arrhythmia and delivery of a high voltage shock may be needlessly long and, further, the voltage or energy may be needlessly excessive. Therefore, a need exists for alternative or adjunct therapies that can treat arrhythmic conditions more quickly and/or at a lesser voltage or energy. Such alternative or adjunct therapies may also reduce patient pain and increase acceptance of certain shock therapies in suitable patient populations. Early conversion of an arrhythmia may also reduce the occurrence of loss of consciousness due to reduced blood flow to the brain. Various exemplary methods, devices, systems, etc., described herein aim to address such needs and/or other needs.

SUMMARY

An exemplary method includes detecting two or more event interval times associated with an arrhythmic condition, averaging event interval times to provide an average event interval time, providing a fraction and calling for delivery of an anti-arrhythmia shock at a delivery time based on the fraction and the average event interval time. In this exemplary method, the events optionally correspond to early coarse ventricular fibrillation events and the delivery time is optionally less than about three seconds from detecting a first event of a first event interval time. Other exemplary methods, devices, systems, etc., are also disclosed.

BRIEF DESCRIPTION OF THE DRAWINGS

Features and advantages of the described implementations can be more readily understood by reference to the following description taken in conjunction with the accompanying drawings.

DETAILED DESCRIPTION

The following description is of the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Overview

Various exemplary mechanisms aim to deliver early and/or low voltage shock anti-arrhythmia therapy. Described below are an exemplary implantable device, various arrhythmic or pre-arrhythmic behaviors, exemplary circuits for use in early and/or low voltage shock therapy, exemplary methods for determining shock therapy parameters and/or delivering shock therapy, and an exemplary plot of early shock average interval fraction versus average interval.

Exemplary Stimulation Device

The techniques described below are intended to be implemented in connection with any stimulation device that is configured or configurable to stimulate and/or shock a patient's heart.

Figure 1:
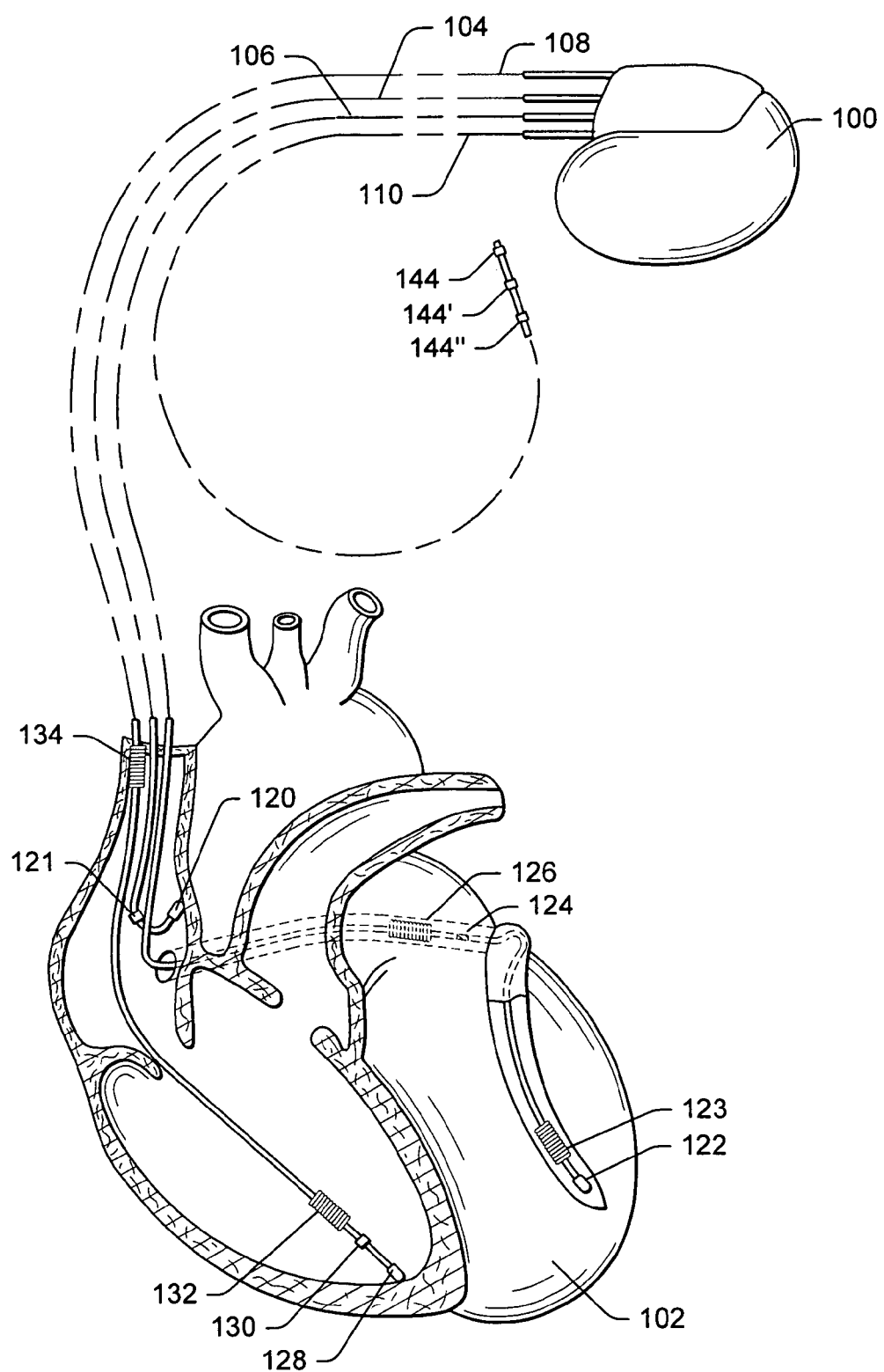
FIG. 1 is a simplified diagram illustrating an exemplary implantable stimulation device in electrical communication with at least three leads implanted into a patient's heart and at least one other lead for sensing and/or delivering stimulation and/or shock therapy. Of course, fewer or more leads may be suitable.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of nerves and/or non-cardiac tissue. In addition, the device 100 includes a fourth lead 110 having, in this implementation, three electrodes 144, 144', 144'' suitable for stimulation and/or detection of physiologic signals that may be used by the implanted system to modify therapy parameters. This lead may be positioned in and/or near a patient's heart or near a tissue within a patient's body and remote from the heart.

The right atrial lead 104, as the name implies, is positioned in and/or passes through a patient's right atrium. The right atrial lead 104 optionally senses atrial cardiac signals and/or provides right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation and/or sensing.

To sense atrial cardiac signals, ventricular cardiac signals and/or to provide cardiac therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular stimulation therapy using, for example, at least a left ventricular tip electrode 122, left atrial stimulation therapy using at least a left atrial ring electrode 124, and stimulation therapy using at least a left atrial coil electrode 126. Coil electrodes are often used for shock therapy. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 may further include bifurcations or legs. For example, an exemplary coronary sinus lead includes stimulation electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve. Such an electrode may be positioned on the lead or a bifurcation or leg of the lead.

The stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include an electrode positioned on a bifurcation or leg of the lead.

Figure 2:
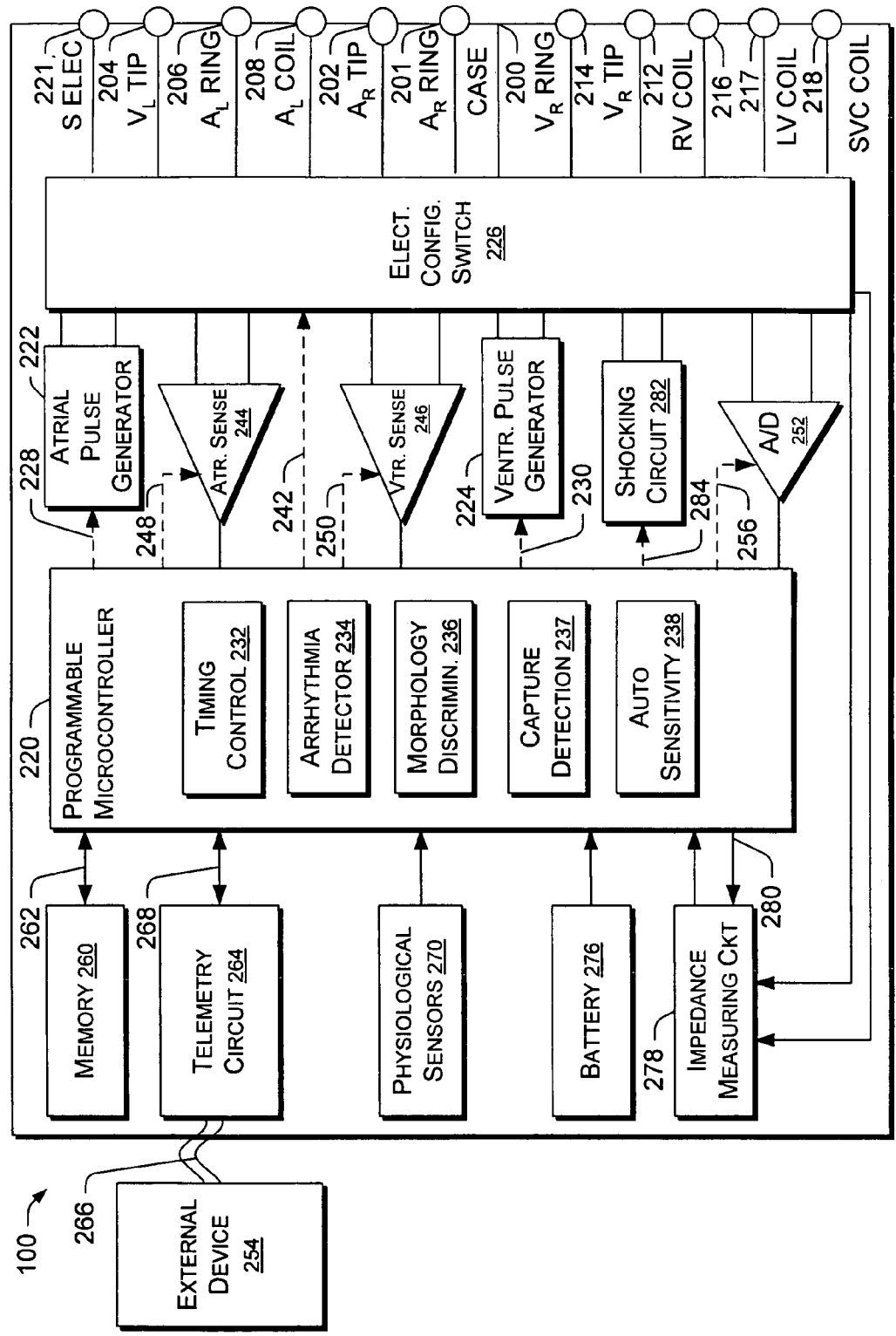
FIG. 2 is a functional block diagram of an exemplary implantable stimulation device illustrating basic elements that are configured to provide cardioversion, defibrillation, pacing stimulation and/or other tissue and/or nerve stimulation. The implantable stimulation device is further configured to sense information and administer stimulation responsive to such information.

FIG. 2 shows an exemplary, simplified block diagram depicting various components of the stimulation device 100. The stimulation device 100 can be capable of treating both fast and slow arrhythmias with stimulation therapy, including cardioversion, defibrillation, and pacing stimulation. The stimulation device 100 may also deliver therapy according to various mechanisms disclosed herein. While a particular multi-chamber device is shown, it is to be appreciated and understood that this is done for illustration purposes only. Thus, the mechanisms (e.g., methods, devices, systems, etc.) described below can be implemented in connection with any suitably configured or configurable stimulation device. Accordingly, given the description herein, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, shock stimulation, etc.

Housing 200 for the stimulation device 100 is often referred to as the "can", "case" or "case electrode", and may be programmably selected to act as a return electrode for all "unipolar" modes (e.g., unipolar electrode configurations). Housing 200 may further be used as a return electrode alone or in combination with one or more of the coil electrodes 126, 132 and 134 for shocking purposes. As described herein other electrodes (coil or other) are optionally used to deliver shock therapy. Housing 200 further includes a connector (not shown) having a plurality of terminals 201, 202, 204, 206, 208, 212, 214, 216, 217, 218, 221 (shown schematically and, for convenience, the names of the electrodes to which they are connected are shown next to the terminals).

To achieve right atrial sensing and/or stimulation, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing and/or stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes is also possible via these and/or other terminals (e.g., via a stimulation terminal S ELEC 221). The stimulation terminal S ELEC 221 may also allow for sensing per appropriate connections or switching.

To support right chamber sensing and/or stimulation, the connector further includes a right ventricular tip terminal ($V_R$ TIP) 212, a right ventricular ring terminal ($V_R$ RING) 214, a right ventricular shocking terminal (RV COIL) 216, a left ventricle shocking terminal (LV COIL) 217 (e.g., for an optional LV coil or other electrode), and a superior vena cava shocking terminal (SVC COIL) 218, which are adapted for connection to the right ventricular tip electrode 128, right ventricular ring electrode 130, the RV coil electrode 132, an optional LV coil electrode (not shown in FIG. 1), and the SVC coil electrode 134, respectively. Connection to suitable autonomic nerve stimulation electrodes is also possible via these and/or other terminals (e.g., via the stimulation terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to nerves, other tissue, etc.) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrioventricular (AV) delay, interatrial conduction (AA) delay, or interventricular conduction (VV) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234. The detector 234 can be utilized by the stimulation device 100 for determining desirable times to administer various therapies. The arrhythmia detector 234 may be implemented in hardware as part of the microcontroller 220, or as software/firmware instructions programmed into the device and executed on the microcontroller 220 during certain modes of operation.

Microcontroller 220 further includes a morphology discrimination module 236, a capture detection module 237 and an auto sensing module 238. These modules are optionally used to implement various exemplary recognition algorithms and/or methods presented below. The aforementioned components may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 may utilize the atrial and ventricular sensing circuits, 244 and 246, to sense cardiac signals to determine whether a rhythm is physiologic or pathologic. The arrhythmia detector 234 may receive such signals or processed signals and determine whether an arrhythmic condition exists, is likely to exist and/or is imminent. Of course, other sensing circuits may be available depending on need and/or desire. In reference to arrhythmias, as used herein, "sensing" is reserved for the noting of an electrical signal or obtaining data (information), and "detection" is the processing (analysis) of these sensed signals and noting the presence of an arrhythmia or of a precursor or other factor that may indicate a risk of or likelihood of an imminent onset of an arrhythmia.

The exemplary arrhythmia detector module 234 optionally uses timing intervals between sensed events (e.g., P-waves, R-waves, and depolarization signals associated with fibrillation which are sometimes referred to as "F-waves" or "Fib-waves") to perform one or more comparisons to a predefined rate zone limit (i.e., bradycardia, normal, low rate VT, high rate VT, and fibrillation rate zones) and/or various other characteristics (e.g., sudden onset, stability, physiologic sensors, and morphology, etc.) to determine a type of remedial therapy (e.g., anti-arrhythmia, etc.) that is desired or needed (e.g., bradycardia pacing, anti-tachycardia pacing, cardioversion shocks or defibrillation shocks, collectively referred to as "tiered therapy"). The exemplary arrhythmia detector 234 may also receive information from a physiologic sensor(s) 270, which may include a hemodynamic sensor, for example, as described below.

Similar rules can be applied to the atrial channel to determine if there is an atrial tachyarrhythmia or atrial fibrillation with appropriate classification and intervention. Such a module is optionally suitable for performing various exemplary methods described herein. For example, such a module optionally allows for analyses related to action potentials (e.g., MAPs, T waves, etc.) and characteristics thereof (e.g., alternans, activation times, repolarization times, derivatives, etc.).

Detection techniques for heart condition that may be suitable for use with various exemplary methods, devices, systems, etc., disclosed herein include those of U.S. patent application Ser. No. 10/848,853, now U.S. Pat. No. 7,225,014 entitled "Anti-arrhythmia Therapy Based on Spatial and/or Temporal Information" to Province; and International PCT Application Serial No. PCT/SE03/00338 (WO 03/071945 A1), entitled "Medical Device" to Noren, which is incorporated by reference herein.

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve stimulation lead through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

As already mentioned, the stimulation device 100 can further include one or more physiologic sensor(s) 270. A commonly used physiologic sensor is a "rate-responsive" sensor that is typically used to adjust pacing stimulation rate according to the exercise state of the patient. However, the physiological sensor(s) 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various parameters (such as rate, AV Delay, V-V Delay, etc.) at which the atrial and ventricular pulse generators, 222 and 224, generate stimulation pulses.

While shown as being included within the stimulation device 100, it is to be understood that the physiologic sensor(s) 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

More specifically, the physiological sensor(s) 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 µA), and is capable of providing high-current pulses (for capacitor charging) when the patient requires a shock or other stimulation pulse, for example, according to various exemplary methods, systems and/or devices described below. The battery 276 also desirably has a predictable discharge characteristic so that elective replacement time can be determined a priori or detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it may detect occurrence of an arrhythmia, and automatically apply an appropriate therapy to the heart aimed at terminating the detected arrhythmia and converting the heart back to a normal sinus rhythm. To this end, the microcontroller 220 further controls a shocking circuit 282 by way of a control signal 284. The shocking circuit 282 is presented as an example herein as other exemplary circuits are discussed below for charging and/or discharging stored charge.

In this example, the shocking circuit 282 can generate shocking or stimulation pulses of low (e.g., up to approximately 0.5 J), moderate (e.g., approximately 0.5 J to approximately 10 J), or high energy (e.g., approximately 11 J to approximately 40 J), as controlled by the microcontroller 220. The aforementioned ranges are representative of conventional ranges and various ranges are discussed further below wherein "low voltage" or "low energy" shocks may extend into the lower end of the aforementioned moderate energy range.

Various other mechanisms are described herein whereby an early shock may be delivered in response to an arrhythmic condition or a condition indicative of an arrhythmia. Such early shock mechanisms typically delivery a shock at an energy from approximately 0.1 J to approximately 5.0 J. In some examples, leading edge voltages for such early shocks range from approximately 50 V to approximately 300 V.

In general, shocking pulses are applied to the patient's heart 102 through at least two electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Conventional cardioversion level shocks are generally considered to be of low to moderate energy level and synchronized with an R wave and/or pertaining to the treatment of tachycardia. In tiered therapy, a "low energy" or "low level" cardioversion tier is normally considered a first-line treatment for ventricular tachycardia (e.g., rates of over approximately 180 bpm). In conventional cardioversion therapy, synchronous QRS complex or R wave delivery aims to avoid delivery of energy during a vulnerable period of the T wave, which may initiate or accelerate transition to ventricular fibrillation.

Defibrillation shocks are generally of a moderate to a high energy level (e.g., corresponding to thresholds in the range of approximately 5 J to approximately 40 J) and a first-line treatment for ventricular fibrillation. If any recognizable QRS complex or R wave exists, or if atrial pacing is present, a defibrillation shock may be delivered synchronously. Accordingly, the microcontroller 220 is capable of controlling the synchronous or asynchronous delivery of the shocking pulses.

Cardiac Rhythms

Figure 3:
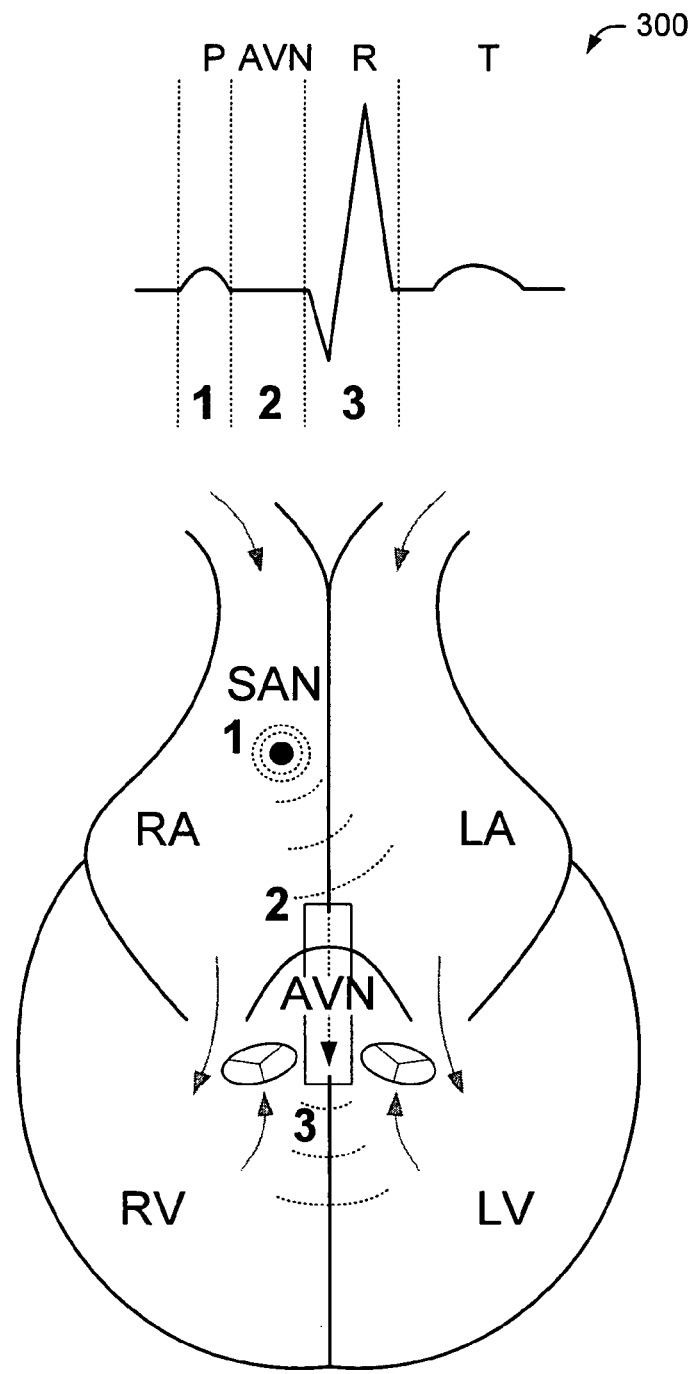
FIG. 3 is an approximate anatomical diagram of a heart and a waveform or ECG.

FIG. 3 shows an approximate anatomical diagram of a heart and an intrinsic waveform 300. Electrical activation propagating through a normal heart is labeled as follows: 1, associated with the sinoatrial node (SAN) and the atria; 2, associated with the atrioventricular node and/or atrioventricular bundle (AVN); and 3, associated with the ventricles. In a normal heart, cells of the SAN (1) spontaneously depolarize and thereby initiate an action potential (shown as dashed lines emanating from the SAN). This action potential propagates rapidly through the atria (which contract), slowly through the AVN (2) and then to the ventricles (3), which causes ventricular contraction. Thus, in a normal heart, ventricular rhythm relies on conduction of action potentials through the AV node and AV bundle (collectively referred to as the AV node or AVN).

An ECG of normal heart activity (e.g., polarization, depolarization, repolarization, etc.) typically shows atrial depolarization as a "P wave", ventricular depolarization as an "R wave", or QRS complex and ventricular repolarization as a T wave. The time span between a P wave and an R wave typically depends on AVN conduction and/or heart rate (e.g., rate of SAN). An ECG may also allow for determination of a QT interval, for example, measured from onset of a QRS complex to the end of ventricular repolarization (e.g., end of T wave). Yet further, an ECG may allow for determination of a ST interval, for example, measured from the end of a QRS complex to the end of a ventricular repolarization.

Ventricular Arrhythmias

Ventricular arrhythmia is a leading cause of sudden cardiac death. Detection of ventricular arrhythmia and/or precursors thereto can help in prevention of such deaths. The aforementioned exemplary implantable cardiac device 100 includes an ability to detect arrhythmia and/or precursors thereto and to respond to such detection. One particular response includes delivery of one or more stimuli to the heart. In general, such stimuli are referred to herein as "low voltage" stimuli or shocks as opposed to high voltage stimuli or shocks commonly associated with defibrillation.

Ventricular arrhythmias often involve reentry wavefronts or circuits that travel around poorly conducting or unresponsive cardiac scar tissue or that travel in a wholly functional myocardial region. Spatial information may help determine locations of such reentry circuits (e.g., their spatio-temporal characteristics). Some studies of pacing to terminate ventricular arrhythmias suggest pacing or delivering stimulation at a site wherein the position of the site is based on location of a reentry circuit. Various studies suggest pacing or delivering at a site proximate to the reentry circuit while others suggest pacing or delivering at a site removed from the reentry circuit. Of course, sometimes pacing or delivering is limited to a single site; consider, for example, an implantable cardiac device having a single lead with a pacing electrode positioned in a patient's right ventricle. In such instances, spatial and/or temporal information pertaining to a reentry circuit may prove beneficial, for example, in determining a pacing time and/or pacing amplitude, frequency, etc. As described herein, such information optionally includes information regarding homogeneity or heterogeneity of a reentry circuit. Further, characteristics of a reentry circuit optionally include information regarding ischemia, conduction velocity, etc.

Various factors may affect successful termination of a ventricular arrhythmia. Such factors include, but are not limited to, arrhythmia rate (e.g., path length and conduction velocity), refractory period at a pacing or stimulation site and/or in a reentry circuit, conduction path from pacing or stimulation site to a reentry circuit (e.g., including conduction velocity, conduction time, etc.), reentry circuit gap characteristics. See, e.g., Sinha, et al., "Critical role of inhomogeneities in pacing termination of cardiac reentry", *CHAOS*, 12(3): 893-902 (2002).

Figure 4:
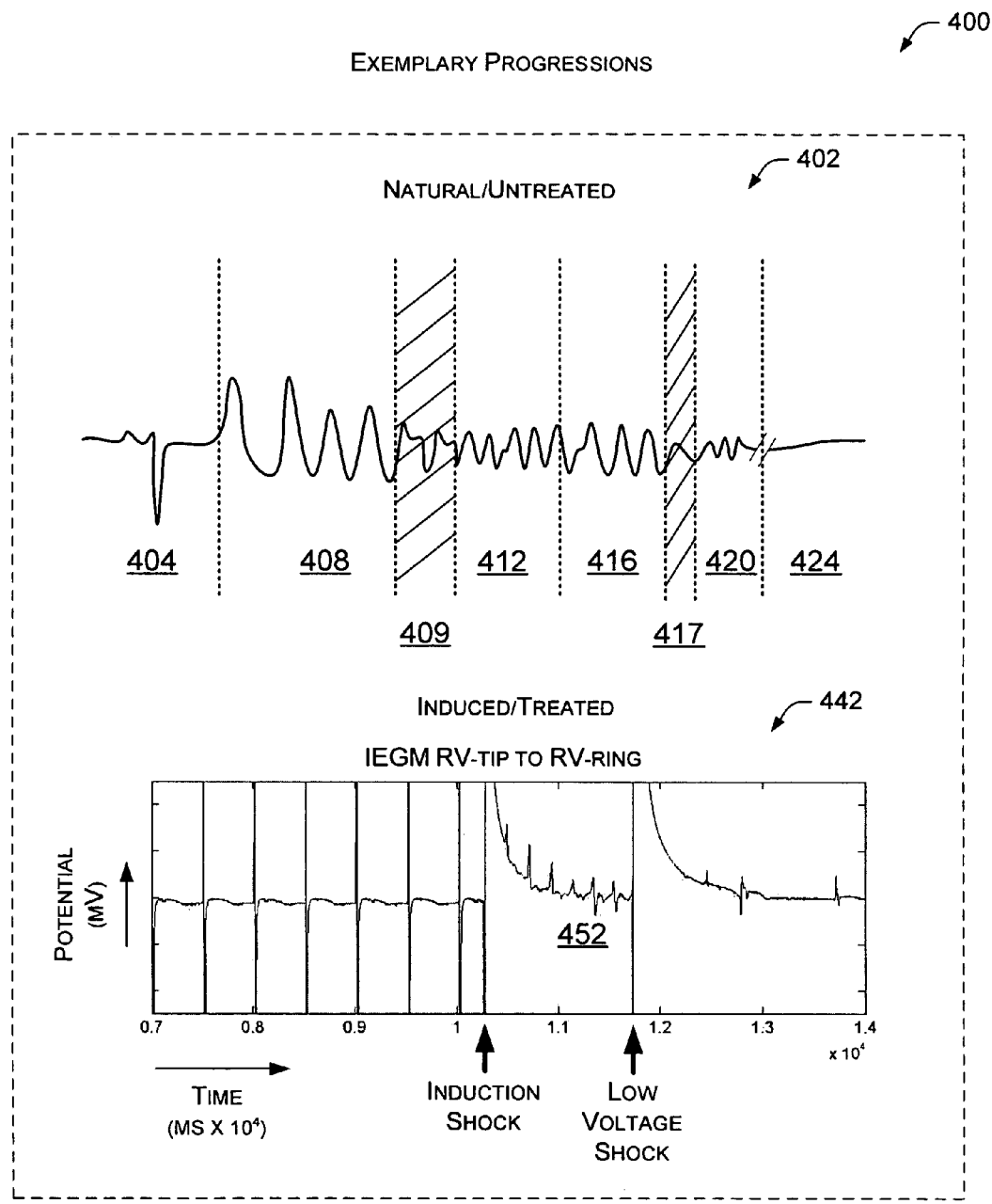
FIG. 4 is a plot of various natural/untreated cardiac waveforms in an exemplary progression of worsening cardiac condition and a plot of various induced/treated cardiac waveforms.

FIG. 4 shows cardiac waveforms of exemplary progressions of worsening cardiac condition 400. The particular progressions shown may vary in form, scale, etc. A first progression 402 represents a natural and untreated progression of worsening cardiac condition that includes arrhythmias (see, e.g., Weiss et al., "Ventricular Fibrillation: How Do We Stop the Waves from Breaking?", *Circ Res.* 2000; 87:1103-1107). Various vertical dashed lines separate or designate regions that include a normal sinus region 404, a region 408 of early organized activation having at least some characteristics associated with or indicative of ventricular tachycardia, a transition region 409 of more complex morphology and typically a decreased interval that may be associated with or indicative of ventricular fibrillation (VF), an early, coarse ventricular fibrillation (VF) region 412, a later, coarse ventricular fibrillation (VF) region 416 (e.g., may be observed in ischemia induced arrhythmia onset), a coarse to fine ventricular fibrillation (VF) region 417, a fine ventricular fibrillation (VF) region 420 and an asystole region 424.

While the exemplary progression 402 is shown with cardiac waveforms of electrical behavior, a similar progression may be noted using other signals. For example, a hemodynamic sensor may detect hemodynamic behavior that indicates compromised cardiac performance. Thus, a hemodynamic sensor may indicate whether a condition is hemodynamically stable or hemodynamically unstable. Such a sensor may be used in conjunction with intracardiac electrograms. Further, intracardiac electrograms, hemodynamic signals, etc., may be analyzed using morphology or other techniques.

A second progression 442 represents an induced and treated progression wherein induction of arrhythmia occurs via a shock administered during a T wave and treatment occurs via an exemplary low voltage shock administered in an arrhythmic region 452. Waveforms in the progression 442 were acquired in a canine trial wherein sensing occurred using a right ventricular tip electrode (see, e.g., the electrode 128 of FIG. 1) and a right ventricular ring electrode (see, e.g., the electrode 130 of FIG. 1). In this example, the region 452 corresponds substantially to the region 408 of early organized activation having at least some characteristics associated with or indicative of ventricular tachycardia and/or the transition region 409 of more complex morphology and typically a decreased interval that may be associated with or indicative of ventricular fibrillation (VF). In this example, delivery of the low voltage treatment shock occurred about 1.5 seconds after the induction shock and at about 80% of the average interval of the prior three RV-sensed intervals. In one example, a shock with energy of approximately 1.7 joules and a leading edge voltage of about 180 volts for a biphasic pulse (about 8 ms) was delivered to a load of about 50 ohms to successfully terminate an arrhythmia. An exemplary method includes delivering an early shock (e.g., within a few seconds of indicia of an arrhythmia) with a leading edge voltage of less than approximately 200 volts to terminate an arrhythmia.

Should irregular beats persist, cardiac condition may be classified as ventricular tachycardia (VT), for example, where three irregular beats of ventricular origin exist with a rate in excess of approximately 100 beats per minute. In general, cardiac waveforms appear abnormal for VT and QRS complexes are often difficult to define. VT waveforms may exhibit "notching" and a broad QRS-like segment (e.g., occurring over approximately 120 ms or more). Further, ST segment and T wave typically exhibit opposite polarity compared to a normal QRS. While the sinus node may be depolarizing normally, there is usually complete AV dissociation and P waves may be observed between the QRS-like segments. Ventricular rhythm during VT is somewhat regular and at a rate greater than approximately 100 bpm and generally less than approximately 220 bpm.

A patient may tolerate some degree of VT; however, VT can be associated with life-threatening hemodynamic malfunction. Sometimes, treatment of VT involves drugs such as lidocaine, procainamide, bretylium tosylate, etc. As mentioned above, an implantable device, upon detection of ventricular tachycardia, may act or respond by delivering a cardioversion stimulus. A cardioversion stimulus of an implantable device typically has an energy level less than approximately 10 joules. For example, a study by Bardy et al., "A prospective randomized repeat-crossover comparison of antitachycardia pacing with low-energy cardioversion", *Circulation*, 87:1889-1896 (1993), used up to four therapeutic attempts of low-energy cardioversion beginning with a 0.2 J pulse wherein, if ineffective, pulse energy was increased to 0.4, 1.0, and finally 2.0 J. Of course, an alternative therapy or therapy tier may occur prior to delivery of a cardioversion stimulus. Such alternative therapies may include anti-tachycardia pacing, which typically rely on energy levels that approximate those used in pacing.

Various exemplary methods, devices, systems, etc., described herein pertain mainly to defibrillation shock therapy and, in particular, to alternative and/or adjunct shock therapies.

As mentioned in the exemplary progressions 400 of FIG. 4, early, coarse ventricular fibrillation (VF) can follow VT, for example, where VT does not subside or otherwise convert back to a normal sinus rhythm. A transition region typically exists between VT and early, coarse VF, wherein rhythm becomes increasingly irregular and waveforms begin to vary in size and shape. In general, VF is characterized by varying degrees of disorganized depolarization and repolarization of multiple areas within one or both ventricles. Since no significant organized depolarization exists, the ventricles do not contract as a unit. Indeed, gross visual observations during VF often describe the myocardium as quivering. Cardiac output during VF is minimal and inadequate. Of course, an implantable device may detect and possibly record early arrhythmic stages of VT.

As described herein, various exemplary devices, systems and methods aim to terminate VF at the early, coarse stage. For example, an early, coarse stage of VF may be defined by a number of intervals. Upon detection of an early, coarse stage of VF, an implantable device may act or respond by delivering one or more shocks or stimuli to the myocardium. Such early, coarse VF therapy stimuli may be synchronized and/or unsynchronized and typically delivered at energy levels less than those used for conventional ventricular defibrillation. For example, if an early, coarse stage of VF is defined as less than 10 intervals from detection then such stimuli may be delivered during this stage in an effort to terminate VF and convert back to a normal sinus rhythm or even to a less hazardous VT, which may be treated via other pacing and/or stimulation therapies (e.g., anti-tachycardia pacing, cardioversion, etc.). Such early, coarse VF defibrillation therapy may be a sub-tier of a defibrillation therapy tier.

Moving beyond early, coarse VF, after, for example, a certain set number of intervals, VF may be classified as later, coarse VF. Upon detection of an advanced or later, coarse VF, an exemplary implantable device may act or respond by delivering one or more defibrillation stimuli at appropriate energy levels and appropriate times. Such later, coarse VF defibrillation therapy may be a sub-tier of a defibrillation therapy tier.

Moving beyond later, coarse VF, a coarse VF may transition into fine VF. Fine VF is often indicative of an advanced VF, i.e., a VF somewhat removed from a time of onset. As VF becomes finer, treatment can become more difficult with a lessening probability of success. Upon detection of fine VF, an exemplary implantable device may act or respond by delivering one or more defibrillation stimuli at appropriate energy levels and appropriate times. Such fine VF defibrillation therapy may be a subtier of a defibrillation therapy tier.

As already mentioned, fine VF may transition to asystole, which may be characterized as a total absence of ventricular electrical activity. Since depolarization does not occur, there is no ventricular contraction. Asystole may occur as a primary event in cardiac arrest, or it may follow VF or pulseless electrical activity (PEA).

If a lower voltage therapy can successfully treat a cardiac condition normally treated via a higher voltage therapy, several advantages may be realized. For example, a lower voltage therapy may result in less pain, an energy savings, and/or less risk or occurrence of block (e.g., AV block, bundle branch block or other block). Further advantages may be gain by early delivery of such therapy as well.

Ventricular asystole can occur also in patients with complete heart block. Detection of asystole may be confused with VF; therefore, a detection technique may use more than one measure to distinguish VF and asystole. In general, treatment for asystole differs from treatment for VF. Fine VF should be treated with defibrillation whereas defibrillation during asystole is potentially harmful. Upon detection of asystole, an exemplary implantable device may inhibit defibrillation therapy and/or trigger or communicate a need to a device, a patient or a care provider (e.g., for administration of a drug, such as epinephrine and/or atropine).

Figure 5:
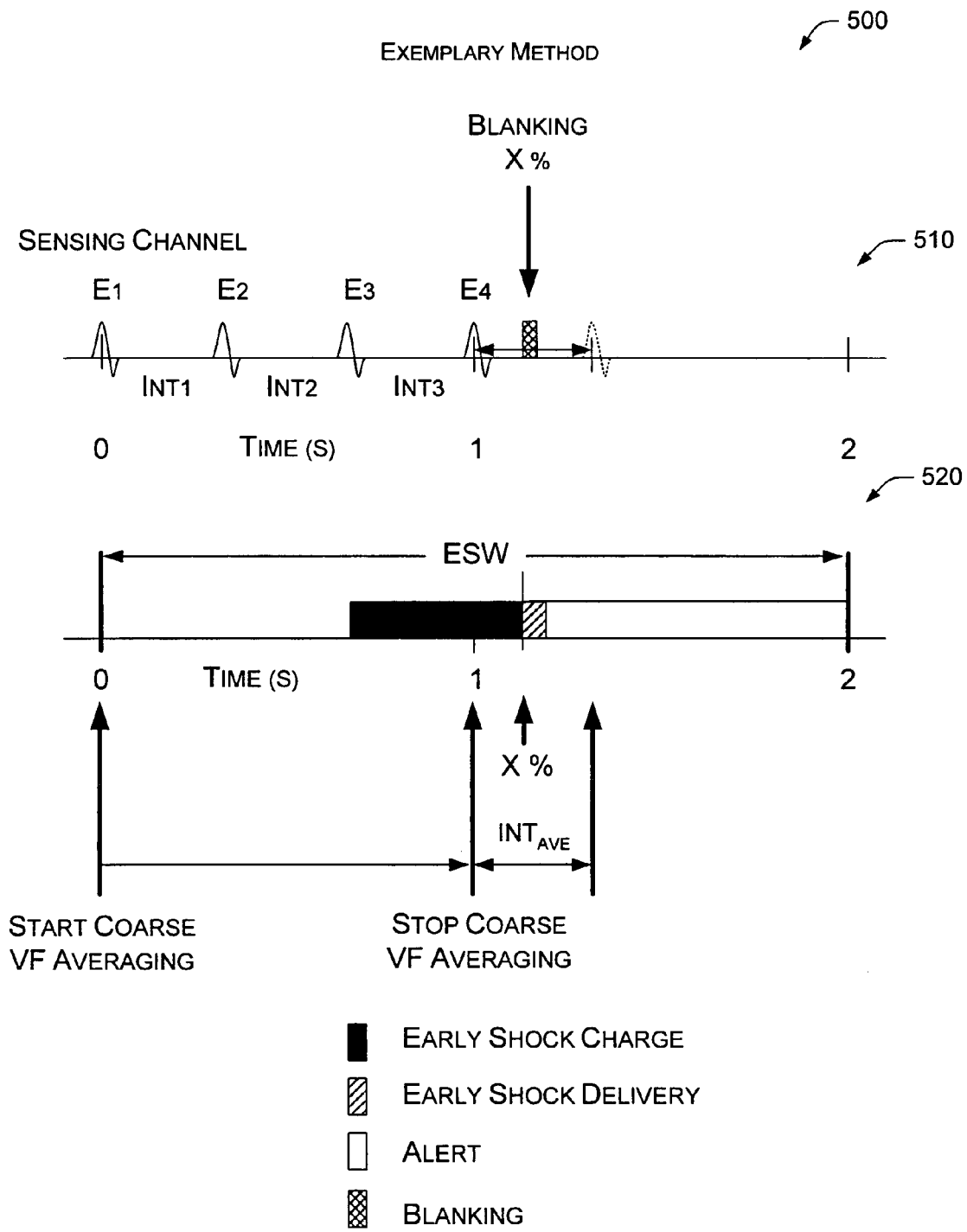
FIG. 5 is a diagram of an exemplary method for delivering an early arrhythmic therapy shock based at least in part on a coarse ventricular fibrillation interval.

FIG. 5 shows an exemplary method 500 for delivering defibrillation therapy. The exemplary method 500 includes determining an average event time interval based on a plurality of coarse ventricular fibrillation events and then delivering a defibrillation shock at a fraction (or percentage) of the average event time interval, for example, after detection of a coarse ventricular fibrillation event.

FIG. 5 shows a sensing channel 510 and an associated window timeline 520 for performing the exemplary method 500. The sensing channel 510 spans approximately 2 seconds wherein from a time of 0 seconds to a time of 1 second, a plurality of events are sensed. In this example, the sensing channel 510 has sensed four events (E1, E2, E3 and E4) or three intervals (Int1, Int2 and Int3). As each subsequent event is sensed, the exemplary method may update an event interval time average and optionally correlate the average to a fraction (or a percentage) for use in timing delivery of a defibrillation early therapy shock. The average is optionally a weighted average that may use one or more forgetting factor, model parameters, etc.

The window timeline 520 includes various exemplary windows that can instruct an implantable device, for example, the device 100 of FIGS. 1 and 2. Such windows may be part of control logic that operates in conjunction with sensed and/or other information (e.g., hardware and/or software implemented). In this example, after a set number of sensed events, a charge window indicates commencement of charging a charge storage unit (e.g., one or more capacitors, etc.). The commencement of charging is optionally based on the number of sensed events, an average event interval time, etc. For example, a shorter interval time may indicate a more localized fibrillation. Accordingly, if electrodes are positioned appropriately, a lesser shock voltage or energy may defibrillate a localized ventricular fibrillation. Thus, in this example, the charge time may be proportional to the average event interval time and/or commence in response to detection of an event indicative of an arrhythmic condition. Referring to the timeline 520, charging commences approximately upon sensing of the third event (E3). Charging may commence at any appropriate time; however, in general, a balance should occur between success of the therapy and wasting energy of an implanted device. For example, charging may commence after detection of a single interval and/or event indicative of an arrhythmic condition. However, such a detection may be less reliable than one that relies on more than one interval and/or event, etc. In one example, charging commences within a charge commencement window (e.g., typically less than about 3 second from detection of a first event or interval indicative of an arrhythmic condition). In some instances the charge time may be determined by the following equation (Eqn. 1):

$$\text{Charge Time} = INT_{AVE} * (N + X\%) \qquad (1)$$

where $INT_{AVE}$ is the average event time interval, N is the number of intervals since charging commenced and X % is the percentage of the interval used for determining when to deliver a defibrillation shock. An exemplary device may optionally monitor charge to ensure that a sufficient charge has accumulated prior to delivery of a shock.

The sensing channel 510 and the timeline 520 indicate delivery of a defibrillation shock at approximately X % of $INT_{AVE}$ after a previously sensed event (E4). In particular, the sensing channel 510 includes a blanking period at a time of approximately $INT_{AVE} * X$ % after sensing of a prior event associated with an arrhythmic condition while the timeline 520 includes a shock delivery window. Further, after the shock delivery window, the timeline 520 includes an alert period window wherein sensing occurs to help determine, for example, if the shock converted the arrhythmia. The alert period window expires after some time upon which a more aggressive shock therapy may occur if desired.

Figure 6:
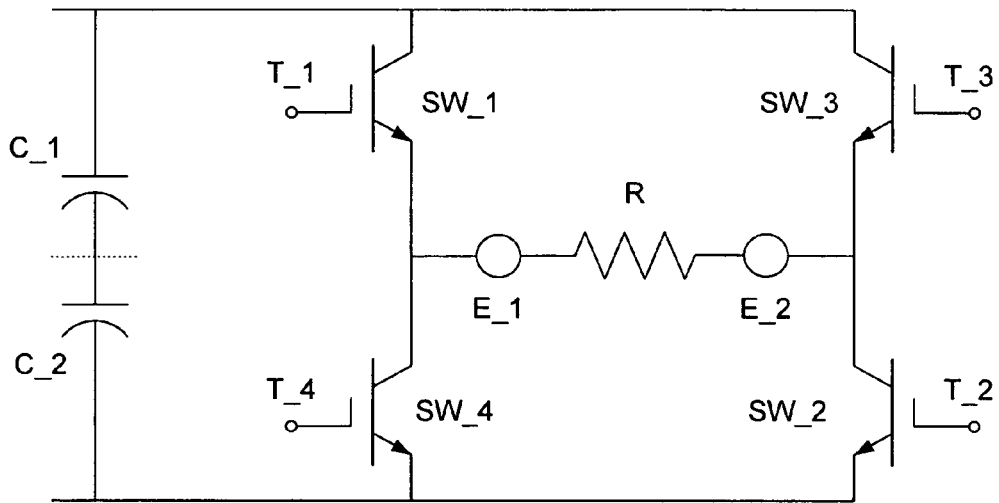
FIG. 6 is a diagram of a conventional system for charging and/or discharging a storage that includes capacitors and an H-bridge.
Figure 6:
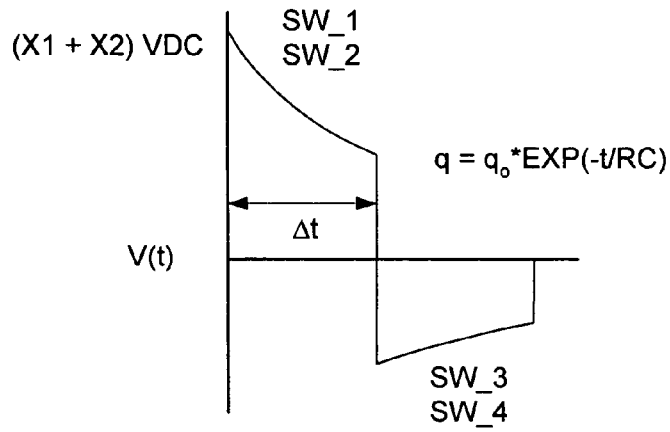

FIG. 6 shows an example of a conventional system 600 for delivering stimulation. Many commercially available implantable defibrillation devices include two capacitors. In such devices, the two capacitors are typically capable of producing approximately 800V when discharged in series.

Capacitors for implantable defibrillation devices are often capable of producing a relatively high voltage, have a relatively high capacitance and of relatively small dimensions and hence volume (e.g., two capacitors may occupy about 8 cubic centimeters). For example, at a volumetric storage capacity of about 4.5 J per cubic centimeter, a total charge of about 30 J would require about 7 cubic centimeters. A commercially available implantable defibrillation device may include two 400 volts direct current (VDC), 188 microfarad (μF) capacitors connected in series to form an equivalent 800 V, 94 μF capacitor. This particular commercially available arrangement is capable of producing a short pulse of approximately 30 joules and approximately 10 milliseconds in duration.

A normal load is approximately 50 ohms, with a typical minimum requirement of approximately 20 ohms. Many commercially available implantable defibrillation devices can charge two capacitors in approximately 6 to approximately 15 seconds, depending upon the discharge state of the battery. With respect to capacitance, many commercially available implantable defibrillation devices use anode foil having a stored energy density of approximately 4 joules to approximately 5 joules per cubic centimeter. Where suitable, other types (size, material, number, etc.) of capacitors may be used in various exemplary methods, devices and/or systems. Other types include, but are not limited to, film dielectric capacitors (e.g., PVDF and polycarbonate), which may include extruded film.

In particular, FIG. 6 shows an example of a conventional circuit 600 that includes a switchable H-bridge 610 connected to two capacitors, C_1 and C_2, and a corresponding discharge curve 620. According to various exemplary methods, devices and/or systems described herein, an exemplary circuit may include a voltage divider circuit controlled via software and/or hardware and capable of reducing voltage to a desired value. In the example of FIG. 6, the H-bridge 610 includes four insulated gate bipolar transistors (IGBTs) labeled SW_1, SW_2, SW_3 and SW_4. Of course, other types of switches may be used in addition to or as alternatives to the IGBT switches and/or other switch configurations may be used. In the switchable H-bridge 610, the switches SW_1, SW_2, SW_3 and SW_4 may be triggered by timing signals received at trigger points labeled T_1, T_2, T_3 and T_4, respectively. The H-bridge includes two electrodes labeled E_1 and E_2, which have a load labeled R, which may represent a patient (e.g., a portion of myocardium, other tissue, etc.). Thus, control of the switches via the trigger points may control discharge of the capacitors labeled C_1 and C_2 across the load R.

Various exemplary circuits allow for simultaneous charge and discharge and/or switching that allows for pseudo-simultaneous charge and discharge (e.g., alternating, etc.). In general, normal charging of the capacitors C_1 and C_2 follows behavior exhibited in the plot 800 of FIG. 8.

Biphasic discharge pulses have proven quite effective in various commercially available implantable defibrillation devices. For example, studies conducted on implantable defibrillation devices have shown that biphasic discharge pulses result in a lower defibrillation threshold when compared to monophasic discharge pulses.

Capacitors typically discharge in a manner that can be suitably modeled by an equation including an exponential decay term. For example, the following equation (Eqn. 2) is used commonly to determine charge with respect to time during discharge:

$$q(t) = q_0 e^{-t/Rc} \quad (2)$$

where q(t), represents charge with respect to time, $q_0$, represents charge at an initial time, R is a resistance or load and C is capacitance (e.g., an RC circuit).

While biphasic pulses have proven useful, other phase pulses are possible and may be used where suitable. In addition, pulses may be truncated, etc. For example, the discharge plot 620 shows voltage (or charge) with respect to time for various switch positions. Upon discharge, switches SW_1 and SW_2 are open while SW_3 and SW_4 are closed for a duration At (also see, e.g., tp). The duration At may be on the order of approximately 2 ms to approximately 6 ms or other suitable time and may be adjustable to suit a particular need. A traditional biphasic pulse may consist of switching switches SW_1 and SW_2 from open to closed while switching switches SW_3 and SW_4 from closed to open (either simultaneously or with a delay). Such a biphasic pulse is often referred to as a truncated biphasic exponential (TBE). Discharge may continue for a time $t_d$, which represents the time at which substantially all of the charge of the capacitors C_1 and C_2 has been discharged (e.g., approximately 99% of $q_0$, etc.). In this example, the capacitors C_1 and C_2 discharge in series.

Figure 7:
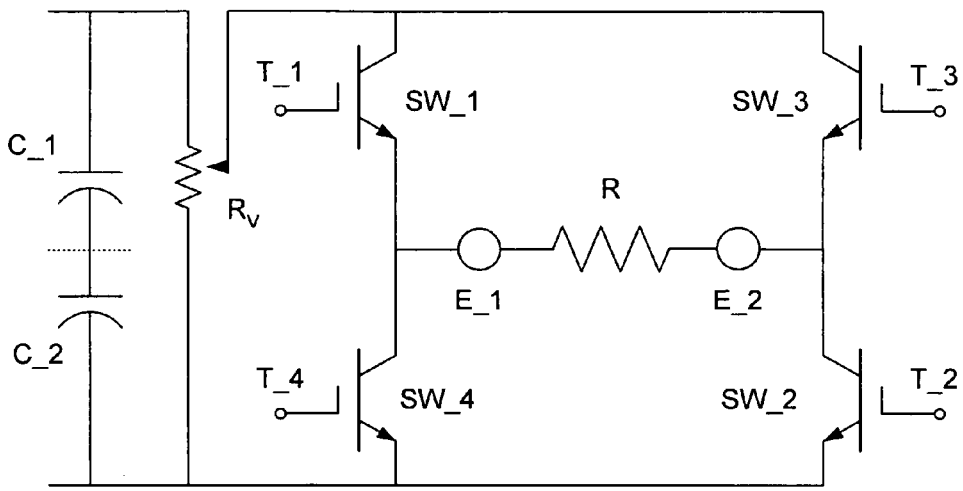
FIG. 7 is an exemplary system for charging and/or discharging a storage that includes capacitors, an H-bridge and a voltage divider.
Figure 7:
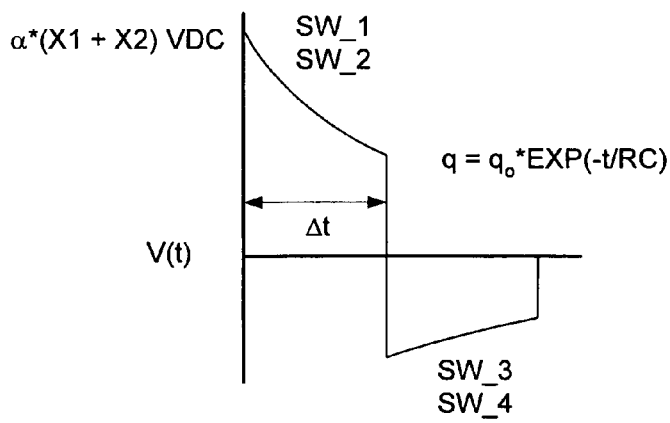

FIG. 7 shows an exemplary circuit 700 that includes a switchable H-bridge 710 connected to two capacitors, C_1 and C_2, a voltage divider $R_V$, and a corresponding discharge curve 720. According to the exemplary circuit 700, the voltage divider circuit is controlled via software and/or hardware and capable of reducing voltage to a desired value. The plot of the discharge curve 720 indicates that the voltage divider may reduce leading edge voltage by a factor α, where α is less than or equal to 1. As in the example of FIG. 6, the H-bridge 710 includes four insulated gate bipolar transistors (IGBTs) labeled SW_1, SW_2, SW_3 and SW_4. Of course, other types of switches may be used in addition to or as alternatives to the IGBT switches and/or other switch configurations may be used. In the switchable H-bridge 710, the switches SW_1, SW_2, SW_3 and SW_4 may be triggered by timing signals received at trigger points labeled T_1, T_2, T_3 and T_4, respectively. The voltage divider may also include one or more trigger points to receive signals to control voltage. The H-bridge 710 includes two electrodes labeled E_1 and E_2, which have a load labeled R, which may represent a patient (e.g., a portion of myocardium, other tissue, etc.). Thus, control of the switches via the trigger points may control discharge of the capacitors labeled C_1 and C_2 across the load R. As described herein, the H-bridge 710 or other circuit connected to a charge storage unit (e.g., one or more capacitors, etc.) may provide for delivery of charge via electrodes configured in a unipolar and/or multipolar arrangement.

Various exemplary circuits allow for simultaneous charge and discharge and/or switching that allows for pseudo-simultaneous charge and discharge (e.g., alternating, etc.). In general, normal charging of the capacitors C_1 and C_2 follows behavior exhibited in the plot 800 of FIG. 8.

Figure 8:
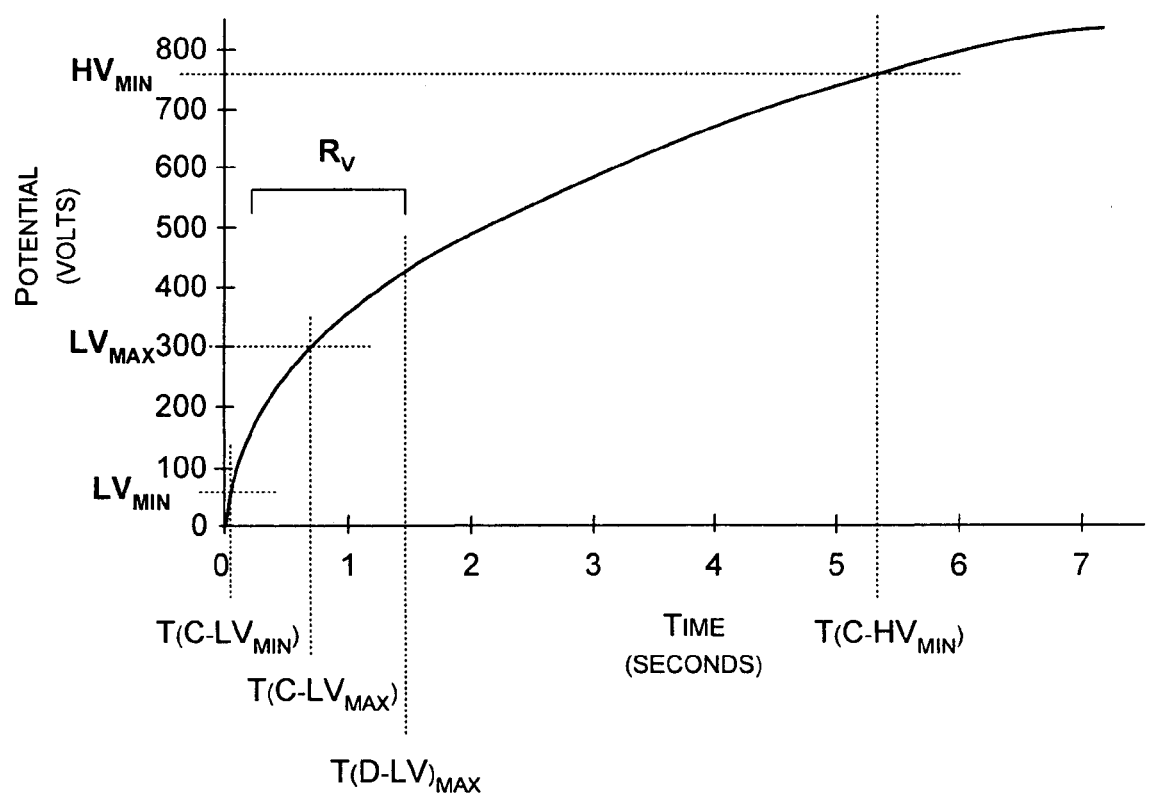
FIG. 8 is a plot of potential versus charge time for a plurality of capacitors.

FIG. 8 shows an exemplary plot 800 of potential in volts versus time in seconds for charging two conventional capacitors such as those described above. The plot 800 includes various exemplary low and high voltage values with corresponding charge times. Tables 1 and 2 include some information related to the plot 800. Table 1 includes potential and charge time information for a charge storage (e.g., one or more capacitors, etc.) at beginning of life (BOL) and at time of recommended replacement (ERI). Table 2 includes energy and charge time for a charge storage at beginning of life (BOL) and at time of recommended replacement (ERI). Table 2 includes information for 10 ms by 10 ms (e.g., 20 ms biphasic cycle) decay and for a 65% tilt. Tilt "k" refers to decay in pulse height typically with respect to a frequency "f" of discharge and/or a pulse length "tp". For example, the following equation (Eqn. 3) may represent tilt:

$$k = \Delta V/V_0 = 0.5 * (1 - e^{-tP/Rc}) \qquad (3)$$

where tp=0.5/f and ΔV corresponds to a decrease in voltage over the time tp and $V_0$ corresponds to an initial voltage.

TABLE 1

Charge Voltage and Charge Time

| Potential (V) | Time-BOL (s) | Time-ERI (s) |
|---|---|---|
| 0 | 0.00 | 0.00 |
| 50 | 0.01 | 0.00 |
| 100 | 0.07 | 0.09 |
| 150 | 0.18 | 0.26 |
| 200 | 0.32 | 0.49 |
| 250 | 0.50 | 0.77 |
| 300 | 0.72 | 1.11 |
| 350 | 0.98 | 1.53 |
| 400 | 1.30 | 2.04 |
| 450 | 1.67 | 2.65 |
| 500 | 2.10 | 3.37 |
| 550 | 2.59 | 4.18 |
| 600 | 3.15 | 5.10 |
| 650 | 3.77 | 6.13 |
| 700 | 4.47 | 7.29 |
| 750 | 5.27 | 8.64 |
| 775 | 5.72 | 9.41 |
| 800 | 6.21 | 10.27 |
| 815 | 6.53 | 10.83 |
| 830 | 6.86 | 11.43 |

TABLE 2

Charge Time and Delivered Energy

| | 10 ms/10 ms | | 65% Tilt | |
|---|---|---|---|---|
| Energy (J) | Time-BOL (s) | Time-ERI (s) | Time-BOL (s) | Time-ERI (s) |
| 0 | 0.00 | 0.00 | 0.00 | 0.00 |
| 2 | 0.36 | 0.55 | 0.36 | 0.00 |
| 4 | 0.72 | 1.10 | 0.71 | 0.54 |
| 6 | 1.08 | 1.68 | 1.08 | 1.09 |
| 8 | 1.47 | 2.30 | 1.45 | 1.66 |
| 10 | 1.86 | 2.96 | 1.85 | 2.27 |
| 12 | 2.27 | 3.64 | 2.25 | 2.91 |
| 14 | 2.69 | 4.34 | 2.68 | 3.57 |
| 16 | 3.13 | 5.06 | 3.11 | 4.25 |
| 18 | 3.57 | 5.78 | 3.55 | 4.94 |
| 20 | 4.03 | 6.53 | 4.00 | 5.65 |
| 22 | 4.50 | 7.31 | 4.47 | 6.39 |
| 24 | 4.98 | 8.14 | 4.95 | 7.14 |
| 25 | 5.23 | 8.57 | 5.20 | 7.94 |
| 26 | 5.49 | 9.02 | 5.46 | 7.94 |
| 27 | 5.76 | 9.48 | 5.73 | 8.35 |
| 28 | 6.03 | 9.95 | 6.00 | 8.77 |
| 29 | 6.32 | 10.43 | 6.28 | 9.21 |
| 30 | 6.62 | 10.90 | 6.58 | 9.67 |
| 31 | 6.95 | 11.35 | 6.88 | 10.61 |

The plot 800 also includes a voltage divider bracket "$R_V$" which represents use of a voltage divider to allow for delivery of a reduced voltage where the potential exceeds a maximum low voltage value "$LV_{max}$". The plot 700 shows a corresponding time "$T(D\text{-}LV_{max})$", which may be a maximum time wherein a voltage divider may be applied. In general, such a voltage divider aims to produce a reduced voltage of at least a minimum low voltage "$LV_{min}$". During operation, the maximum low voltage $LV_{max}$ is achieved at a time "$T(C\text{-}LV_{max})$" and the minimum low voltage $LV_{min}$ is achieved at a time "$T(C\text{-}LV_{max})$". The plot 800 includes a minimum high voltage "$HV_{min}$" and a corresponding time "$T(C\text{-}HV_{min})$".

In general, for a capacitor charge and voltage are related. For example, if two poles of a capacitor are separated by an infinite resistance, the voltage between the poles may be measured and related to charge. Discharge voltage will normally not exceed this voltage, which may be considered a maximum voltage and approximately a leading edge voltage depending on discharge path and/or switching. With respect to energy delivered during a shock, one may consider resistance of a discharge path, discharge time, switching, etc. In an exemplary shocking arrangement, a leading edge voltage of about 50 volts may correspond to a delivered energy of about 0.1 J and a leading edge voltage of about 300 volts may correspond to a delivered energy of about 5 J. In this example, such relationships may vary with respect to physiology (e.g., patient position, respiratory cycle, hydration, etc.).

Figure 9:
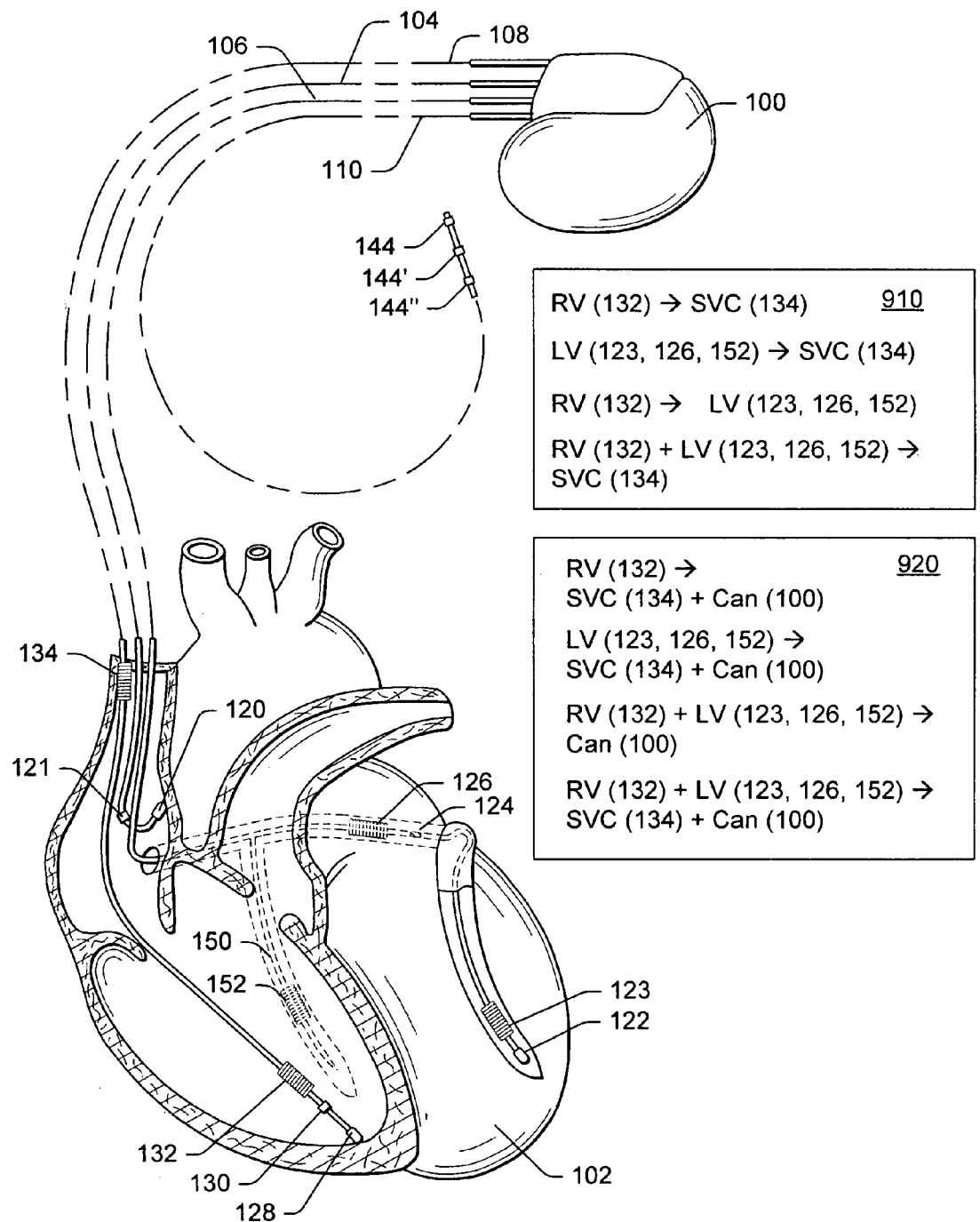
FIG. 9 is a diagram of an exemplary implantable device that includes one or more leads and capable of implementing one or more electrode configurations for early shock therapy.

FIG. 9 shows an approximate diagram of a heart 102 and an exemplary implanted cardiac device 100. The implanted cardiac device 100 includes various electrodes such as those shown in FIG. 1 as well as a few other electrodes. For example, the lead 106 includes a bifurcation 150 that extends into a contributory vessel of the coronary sinus (e.g., middle cardiac vein, etc.) for positioning of a coil electrode 152. The lead 106 also includes another coil electrode 123 capable of being positioned in a contributory vessel of the coronary sinus (e.g., the great cardiac vein, etc.).

FIG. 9 also shows a first set of exemplary electrode configurations 910 that do not include use of a can electrode and a second set of exemplary electrode configurations 920 that include use of a can electrode. The first set of electrode configurations 910 includes:

RV (132)→SVC (134)
LV (123, 126, 152)→SVC (134)
RV (132)→LV (123, 126, 152)
RV (132)+LV (123, 126, 152)→SVC (134)

The second set of electrode configurations 920 includes:

RV (132)→SVC (134)+Can (100)
LV (123, 126, 152)→SVC (134)+Can (100)
RV (132)+LV (123, 126, 152)→Can (100)
RV (132)+LV (123, 126, 152)→SVC (134)+Can (100)

Various exemplary methods, devices and/or systems described herein include use of an electrode configuration that does not include a can electrode (e.g., a multipolar configuration). For example, an exemplary method may call for delivery of an early, low voltage shock using an electrode configuration selected from the first set 910 of electrode configurations. If such a shock does not stabilize cardiac rhythm, then another shock may be called for and delivered using another electrode configuration selected from the first set 910 or the second set 920 of electrode configurations. Such a subsequent shock may have a higher voltage or energy.

Figure 10:
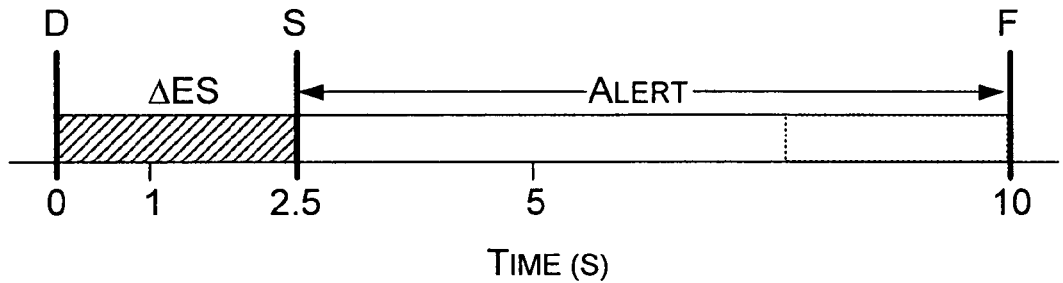
FIG. 10 is a diagram of an exemplary scenario for early shock therapies.

FIG. 10 shows an exemplary scenario 1000 for early shock therapy. The exemplary scenario 1000 is shown along a timeline that includes several windows. A first window, referred to as an early shock window ΔES, spans a period from a determination of a need for a shock (e.g., label D, which may correspond to the detection of a certain number of fast beats and/or hemodynamic sensor information) to an end of the early shock window whereby, for example, a determination has been made to charge a charge storage (e.g., label S) to a level capable of delivering a higher energy or voltage defibrillation shock (e.g., same or similar to a conventional high voltage defibrillation shock, etc.). In general, the early shock window is a few seconds or less in duration. In this example, the early shock window spans about 2.0 seconds and a subsequent alert period spans about 7.5 seconds. According to the exemplary scenario 1000, the charge storage has a charge sufficient to deliver a high voltage defibrillation shock, typically at a time of approximately 10 seconds or less from the time wherein a need for a shock was first determined (e.g., from time D).

Figure 11:
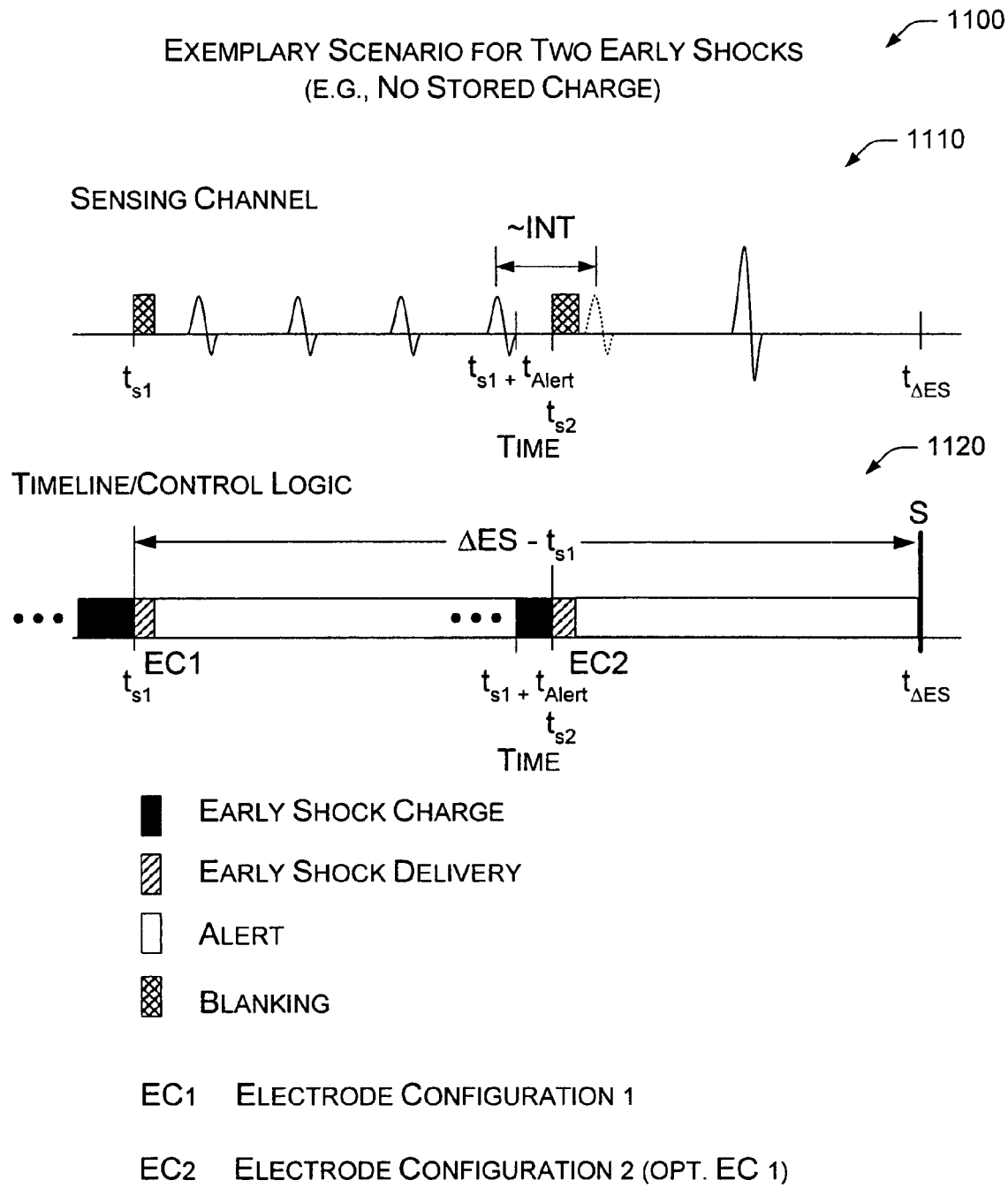
FIG. 11 is a diagram of an exemplary scenario wherein two early shocks are delivered.

FIG. 11 shows an exemplary scenario 1100 wherein more than one early shock is delivered during an early shock window ΔES. The exemplary scenario 1100 includes a sensing channel 1110 and a timeline 1120 that exhibits timing of various windows (e.g., control logic). The sensing channel 1110 and the timeline 1120 include a span from a time $t_{s1}$ to a time $t_{\Delta ES}$. The time $t_{s1}$ corresponds to a delivery time for a first early shock and the time $t_{\Delta ES}$ corresponds to expiration of the early shock window ΔES. As shown, the sensing channel 1110 includes a blanking period at time $t_{s1}$ while the timeline 1120 includes a first early shock delivery window at time $t_{s1}$.

According to the timeline 1120, an alert period window follows the first shock wherein the sensing channel 1110 indicates that the arrhythmia (e.g., coarse ventricular fibrillation) persists. At some point in time, charging commences of a charge storage unit, as appropriate and if needed. For example, the charging may commence upon expiration of the alert period window at a time $t_{s1}+t_{Alert}$, if the first early shock did not succeed.

Next, the exemplary scenario 1100 indicates that a second early shock was delivered at a time $t_{s2}$, wherein the time $t_{s2}$ was determined as a fraction of an average event time interval based on the events sensed during the preceding alert period. A waveform shown with a dotted line indicates where a subsequent coarse ventricular fibrillation event could be expected based, for example, on the average event time interval (~INT). Another alert period follows, as indicated by the alert period window of the timeline 1120. Further, in this scenario, the sensing channel 1110 indicates sensing of a single event only. The occurrence of such a single event during the alert period may indicate that the shock was successful at converting the arrhythmia to a normal or to a less threatening rhythm.

The exemplary scenario 1100 also indicates that the first early shock was delivered using an electrode configuration EC 1 and the second early shock was delivered using an electrode configuration EC 2, which is optionally the same as EC 1. Of course, as mentioned with respect to FIG. 9, an early shock may use any of a variety of electrode configurations, for example, selected from the set 910 and/or the set 920.

Figure 12:
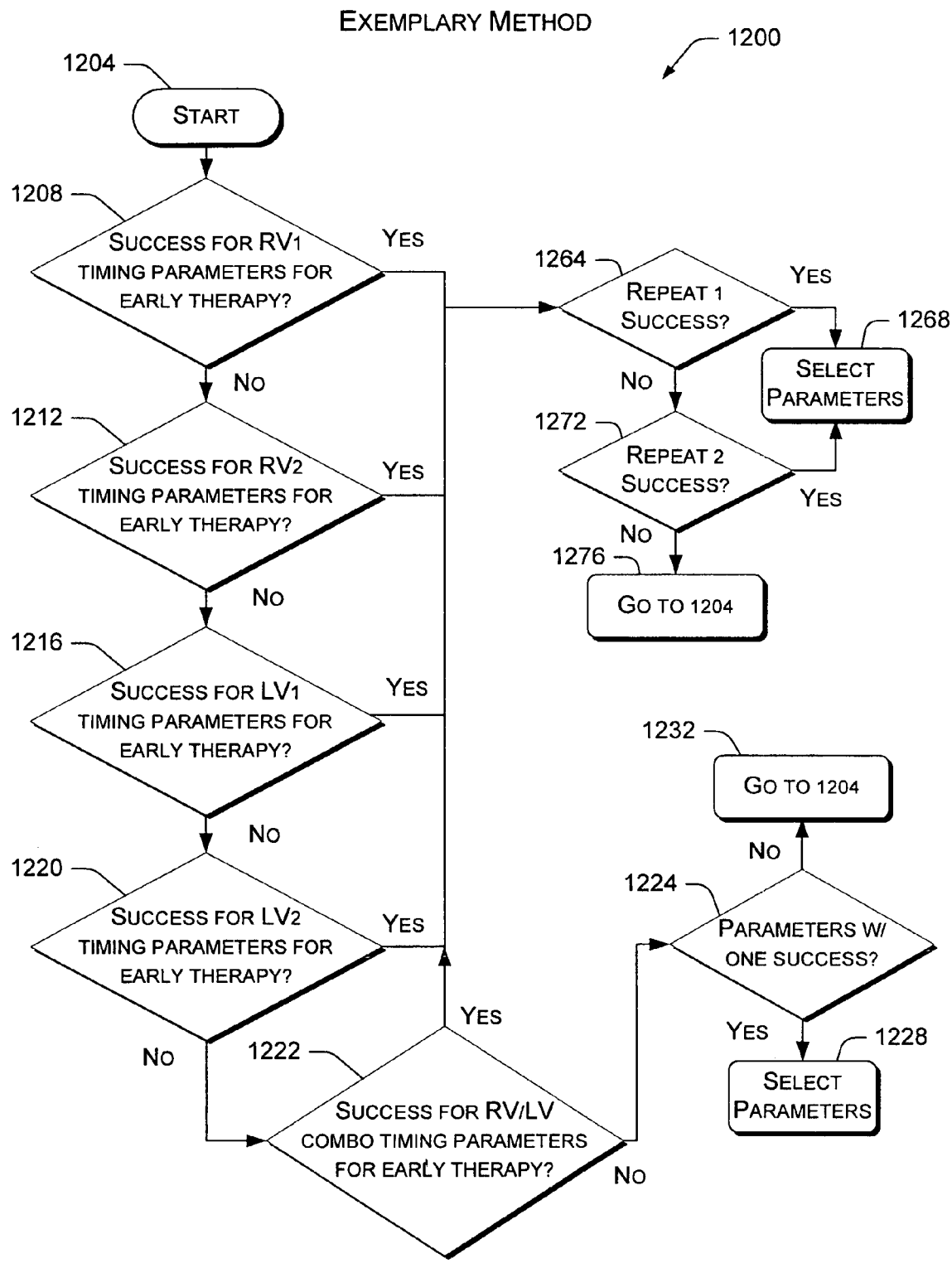
FIG. 12 is a block diagram of an exemplary method for determining therapy parameters.

FIG. 12 shows an exemplary method 1200 for optionally adjusting one or more parameters. The exemplary method 1200 commences in a start block 1204. A series of blocks 1208, 1212, 1216 and 1220 follow the start block 1204 in an order of a first portion of an interval for a right ventricle (RV1) 1208, a second portion of an interval for a right ventricle (RV2) 1212, a first portion of an interval for a left ventricle (LV1) 1216 and a second portion of an interval for a left ventricle (LV2) 1220. The particular order may be different in some other examples and more than two portions, fractions, percentages, etc., may exist for an interval. For example, consider a combination block 1222, which is optional. The combination block 1222 allows for scenarios where a combination of RV and LV portions may be used, for example, LV 10% and RV 80%. In this example, LV may be LV1, LV2, etc., and RV may be RV1, RV2, etc.

In each of the blocks 1208, 1212, 1216, 1220, 1222 a determination is made as to whether delivery of a shock, according to one or more parameters, in that portion of an interval for a particular ventricle or combination of ventricular intervals successfully terminated an arrhythmic condition or condition indicative of an arrhythmia. For example, in the block 1208, a decision occurs as to whether one or more parameters associated with delivery of a shock in a right ventricle successful terminated an arrhythmic condition or condition indicative of an arrhythmia. If the decision block 1208 decides that the treatment was a success, then the method 1200 continues at a subsequent delivery block 1264 that also decides if the subsequent delivery using the same parameters was successful. If the block 1264 decides that the subsequent delivery was successful, then the one or more parameters are selected for use. However, if the subsequent delivery does not succeed, then the method 1200 continues at a second subsequent delivery block 1272. If the second subsequent delivery is successful, then the one or more parameters are selected for use; however, if after two subsequent deliveries success has not been obtained, then the method 1200 continues at the start block 1204 per the go to block 1276 or optionally at one of the other blocks in the series (e.g., 1212, 1216, 1220, 1222). With respect to the other blocks 1212, 1216, 1220, 1222, the method 1200 continues essentially as discussed above for the block 1208. If no success has been obtained after trying each of the blocks 1208, 1212, 1216, 1220 and 1222, then the method continues at a decision block 1224. The decision block 1224 decides if success was obtained for at least one occasion (e.g., using one or more delivery related parameters). If success was obtained for at least one occasion, then the associated one or more parameters for one of the at least one occasion are selected in a selection block 1228. If no such success was obtained, then the method 1200 continues at the start block 1204 per the go to block 1232.

Figure 13:
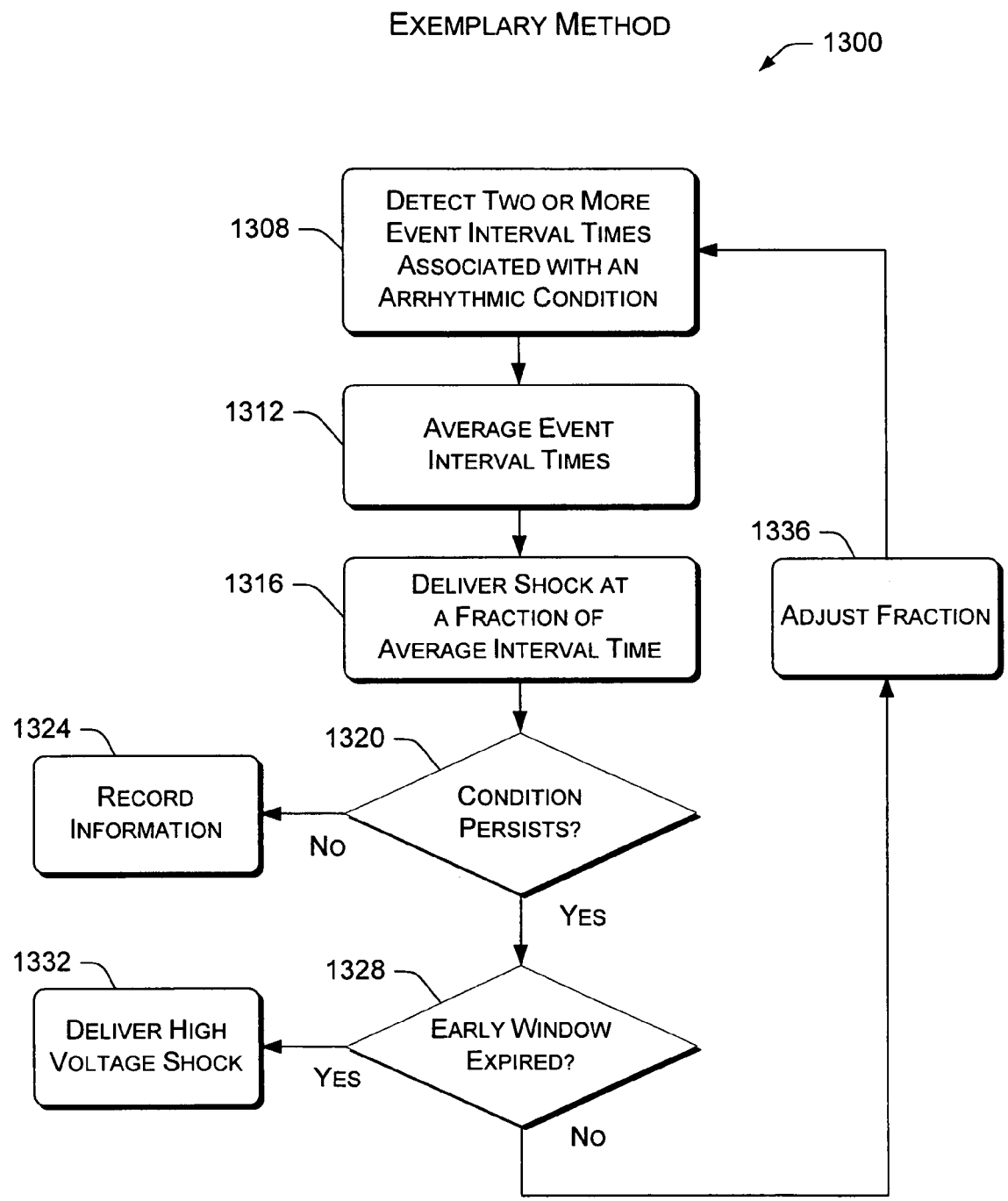
FIG. 13 is a block diagram of an exemplary method for delivering shock therapy.

FIG. 13 shows a block diagram of an exemplary method 1300 for delivering defibrillation shock therapy. The method 1300 commences in a detection block 1308 that detects two or more event interval times associated with an arrhythmic condition. For example, the detection block 1308 may detect a rate or interval times for two or more intervals, a rate or interval times for two or more intervals combined with a morphology change, a rate or interval times for two or more intervals combined with hemodynamic sensor information, etc. The detect block 1308 may detect events and/or intervals defined by events. According to the exemplary method 1300, after the detection block 1308, an average block 1312 averages the intervals. In an alternative example, averaging occurs during the detecting of the events.

In an effort to convert the arrhythmic condition to a more healthy rhythm, a delivery block 1316 follows the average block 1312 wherein delivery of a shock occurs at a fraction (or percentage) of the average interval time (e.g., per block 1312). The shock may include a shock energy value that lies in a range from approximately 0.1 J to approximately 5 J. With respect to voltage, the shock may include a leading edge voltage (or peak voltage) value that lies in a range from approximately 50 volts to approximately 300 volts. As discussed above, one or more parameters may be adjusted in response to success of the delivered shock. Such one or more parameters may account for a plurality of sensing locations for sensing an event or events.

According to the exemplary method 1300, a decision block 1320 then decides if the condition persists. If the condition no longer persists, then a record block 1324 records information (e.g., one or more parameters, etc.)

wherein such information is optionally used in a subsequent therapy and/or to aid in diagnosis of cardiac condition. However, if the condition persists, then another decision block 1328 decides if an early shock window has expired. If the early shock window has expired, then a high voltage therapy delivery block 1332 delivers, for example, a high voltage defibrillation shock at an appropriate later time (e.g., providing that a sufficient stored charge is available).

If the decision block 1328 indicates that sufficient time remains within the early shock window, then the exemplary method 1300 may adjust the fraction in an adjust block 1336 and continue at the detect block 1308. In an alternative exemplary method, an adjust block may adjust electrode configuration, shock phase, shock energy, etc., in lieu of or in addition to adjusting a fraction or a percent.

Figure 14:
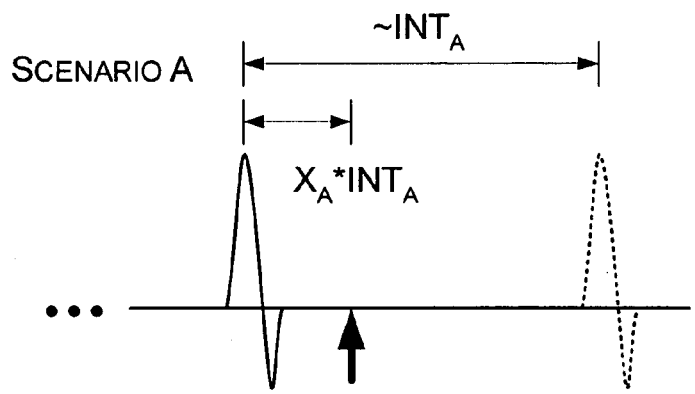
FIG. 14 is a diagram that includes an exemplary plot of fraction versus average event interval time for early shock therapy.
Figure 14:
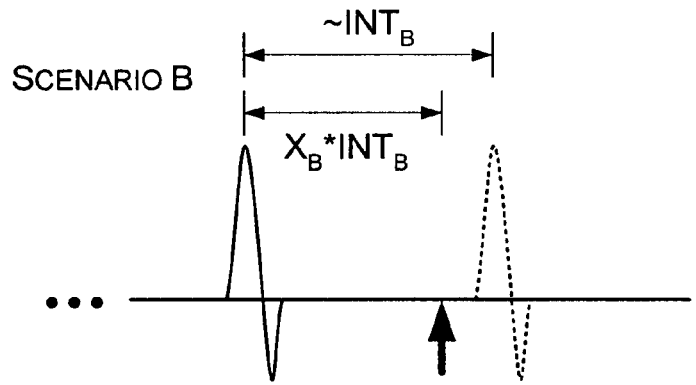
Figure 14:
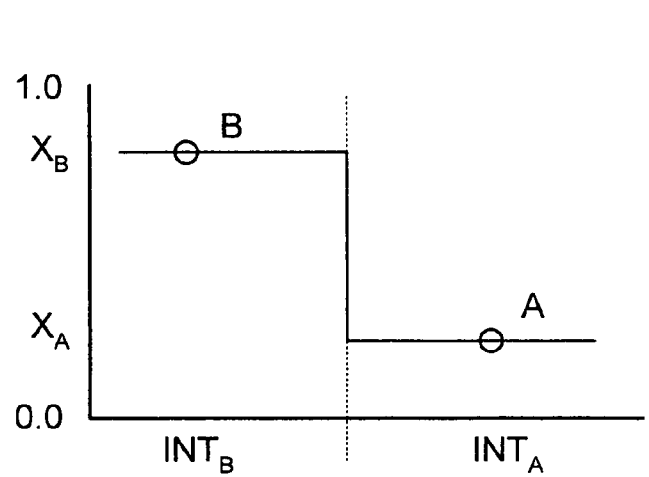

FIG. 14 shows an exemplary method 1400 wherein a correlation exists between average event interval time and fraction of interval for shock delivery. FIG. 14 shows a first sensing channel 1410 corresponding to scenario A and a second sensing channel 1420 corresponding to scenario B. Scenarios A and B differ in that the average interval for scenario A (~$INT_A$) exceeds the average interval for scenario B (~$INT_B$). Further, the optimal fraction for scenario A ($X_A$) is less than the optimal fraction for scenario B ($X_B$). Accordingly, such information may indicate trends for a specific patient or a patient population. An exemplary trend is shown in a plot 1430 of fraction versus average event interval time. The plot 1430 includes data from scenario A and scenario B and indicates that a high fraction exists for short average interval times and a low fraction exists for longer average intervals times. While such a plot may depend on patient, electrode placement, electrode configuration, etc., the information contained within is optionally used for selecting a fraction or percent given an event interval. While the plot 1430 includes a low fraction state and a high fraction state, some other plots, tables, methods, etc., may include more than two states, a curve, etc.

An exemplary method may commence with two possible states (e.g., a low fraction state and a high fraction state) and then analyze results for a particular patient to determine when to use one state and when to use the other state and/or determine whether adjustments to the states may provide better care and/or whether additional states may provide better care (e.g., better success at terminating an arrhythmic condition). In one example, a low fraction state of approximately 10% of an average interval time is used and a high fraction state of approximately 80% of an average interval time is used.

An exemplary method optionally relies on a relationship between information for a first site and information for a second site. For example, a first site may be a sensing site that senses interval time and a second site may be a delivery site that can be used to deliver a shock. Thus, a plot or a table may include a relationship that relates interval time at the first site to a fraction of an interval or a delivery time at the second site. In another example, a weighted average interval time is determined using information from more than one sensing site and, in turn, relied on to arrive at an appropriate fraction for shock delivery.

Figure 15:
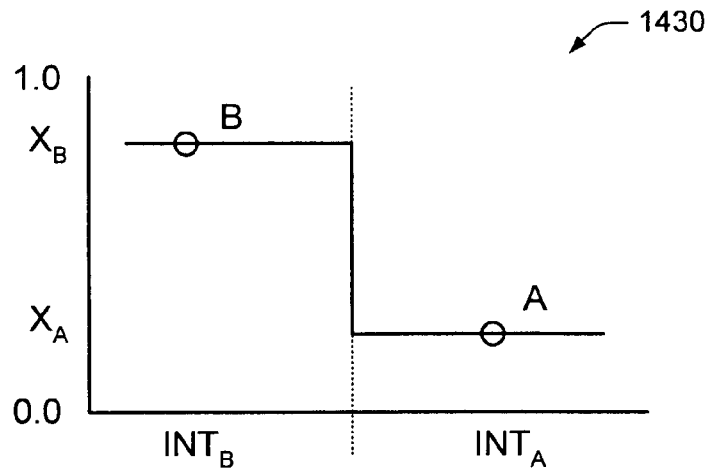
FIG. 15 includes the exemplary plot of FIG. 14 and an exemplary equation to determine an early shock time.

FIG. 15 shows an exemplary method 1500 that includes the plot 1430 of FIG. 14 whereby an exemplary equation 1440 is used to predict an earliest time for delivery of an early shock based on event interval (INT), number of intervals (n) and fraction (X). The event interval may be a single event interval, an average event interval, etc. In general, the fraction (X) depends on the event interval used in the equation 1440. To illustrate use of the equation 1440, two exemplary scenarios 1450 are shown. In scenario A, the interval is about 250 ms, the number of intervals is 3 and the fraction is 0.2. Accordingly, the earliest time for delivery of an early shock is about 800 ms. In scenario B, the interval is about 150 ms, the number of intervals is 3 and the fraction is 0.8. Accordingly, the earliest time for delivery of an early shock is about 570 ms. Such information is optionally used to determine when to start charging, sensing (e.g., alert period), blanking, etc. Such information may be used to decide whether to deliver an early shock. For example, if the time is too long in comparison to an early shock window, then an exemplary implantable defibrillation device may forgo early shock therapy and deliver a later high voltage defibrillation shock.

CONCLUSION

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. A method comprising:
   detecting two or more event interval times associated with an arrhythmic condition;
   averaging event interval times to provide an average event interval time;
   computing a fraction of the event interval time based at least in part on the average event interval time and on one or more fractions associated with past deliveries of anti-arrhythmia shocks; and
   determining a delivery time interval for delivering an anti-arrhythmia shock after a previously sensed event based on the fraction and the average event interval time.

2. The method of claim 1 wherein the events correspond to early coarse ventricular fibrillation events.

3. The method of claim 1 further comprising calling for charging of a charge storage in response to the detecting.

4. The method of claim 1 wherein the anti-arrhythmia shock comprises an energy of less than approximately 5 joules.

5. The method of claim 1 wherein the anti-arrhythmia shock comprises a leading edge voltage of less than approximately 200 volts for a load of approximately 50 ohms.

6. The method of claim 1 wherein the arrhythmic condition corresponds to a ventricular fibrillation.

7. The method of claim 1, wherein the averaging averages less than approximately 10 event intervals.

8. The method of claim 1, further comprising, if the arrhythmic condition persists after the delivery, calling for delivery of a higher energy shock.

9. A method comprising:
   detecting two or more event interval times associated with an arrhythmic condition;
   averaging event interval times to provide an average event interval time;
   computing a fraction of the average event interval time; and
   determining a delivery time interval for delivering an anti-arrhythmia shock after a previously sensed event based on the fraction and the average event interval time wherein the delivery time is less than about three seconds from the detecting of a first event of a first event interval time.

10. The method of claim 9 wherein computing the fraction further comprises computing the fraction based at least in part on one or more fractions associated with past deliveries of an anti-arrhythmia shock.

11. An implantable apparatus comprising:
an input for receiving event information;
a charge storage to store energy;
an output for energy of the charge storage; and
control logic to determine two or more event interval times based on event information associated with an arrhythmic condition, to determine an average event interval time based on the event interval times and a fraction of the average event interval time based at least in part on the average event interval and on one or more previous delivery times, and to determine an anti-arrhythmia shock delivery time interval for delivery of an anti-arrhythmia shock after a previously sensed event based on the fraction of the average event interval time and the average event interval time.

12. The apparatus of claim 11 further comprising a voltage divider operatively connected to the charge storage and the output.

13. The apparatus of claim 12 further comprising control logic to control the voltage divider based at least in part on the delivery time and stored energy of the charge storage.

14. The apparatus of claim 11 further comprising control logic to determine if delivery of the anti-arrhythmia shock at the delivery time terminated the arrhythmic condition.

15. The apparatus of claim 14 further comprising control logic to call for delivery of a higher energy shock if the delivery of the anti-arrhythmia shock at the delivery time failed to terminate the arrhythmic condition.

16. The apparatus of claim 11 further comprising a multiplexer to selectively allow for electrical connection between the output and a plurality of electrodes.

17. The apparatus of claim 11 wherein the delivery time is less than about three seconds from receiving information of a first event of a first event interval time associated with the arrhythmic condition.

18. The apparatus of claim 11 further comprising control logic to call for charging of the charge storage in response to event information indicative of the arrhythmic condition.

19. The apparatus of claim 11 wherein the anti-arrhythmia shock comprises an energy of less than approximately 5 joules.

20. The apparatus of claim 11 wherein the anti-arrhythmia shock comprises a leading edge voltage of less than approximately 200 volts for a load of approximately 50 ohms.

21. A system comprising:
means for detecting two or more event interval times associated with an arrhythmic condition;
means for averaging event interval times to provide an average event interval time;
means for computing a portion of the event interval time based on the average event interval time and on one or more fractions associated with past deliveries of an anti-arrhythmia shock; and
means for delivering an anti-arrhythmia shock at a delivery time interval after a previously sensed event based on the portion and the average event interval time.

* * * * *